United States Patent
Reddy et al.

(10) Patent No.: US 12,252,690 B2
(45) Date of Patent: Mar. 18, 2025

(54) MAMMALIAN CELL LINE FOR PROTEIN PRODUCTION AND LIBRARY GENERATION

(71) Applicant: ETH ZURICH, Basel (CH)

(72) Inventors: Sai Reddy, Basel (CH); William Kelton, Basel (CH); Cristina Parola, Basel (CH); Derek Mason, Basel (CH); Mark Pogson, North Bend, WA (US)

(73) Assignee: ETH ZURICH (CH)

( * ) Notice: Subject to any disclaimer, the term of this patent is extended or adjusted under 35 U.S.C. 154(b) by 4 days.

(21) Appl. No.: 18/329,296

(22) Filed: Jun. 5, 2023

(65) Prior Publication Data

US 2023/0374491 A1 Nov. 23, 2023

Related U.S. Application Data

(63) Continuation of application No. 16/090,829, filed as application No. PCT/EP2017/056373 on Mar. 17, 2017, now Pat. No. 11,802,281.

(30) Foreign Application Priority Data

Apr. 4, 2016 (EP) .................................. 16163734

(51) Int. Cl.
| | | |
|---|---|---|
| C12N 15/10 | (2006.01) | |
| C12N 5/0781 | (2010.01) | |
| C12N 9/22 | (2006.01) | |
| C12N 15/113 | (2010.01) | |
| C40B 10/00 | (2006.01) | |
| C40B 20/04 | (2006.01) | |
| C40B 40/08 | (2006.01) | |

(52) U.S. Cl.
CPC ....... *C12N 15/1037* (2013.01); *C12N 5/0635* (2013.01); *C12N 9/22* (2013.01); *C12N 15/102* (2013.01); *C12N 15/1058* (2013.01); *C12N 15/1082* (2013.01); *C12N 15/1086* (2013.01); *C12N 15/113* (2013.01); *C40B 10/00* (2013.01); *C40B 20/04* (2013.01); *C40B 40/08* (2013.01); *C12N 15/1034* (2013.01); *C12N 2310/20* (2017.05); *C12N 2510/00* (2013.01); *C12N 2510/02* (2013.01); *C12N 2800/80* (2013.01); *C12Q 2521/539* (2013.01)

(58) Field of Classification Search
None
See application file for complete search history.

(56) References Cited

U.S. PATENT DOCUMENTS 11,802,281 B2 * 10/2023 Reddy ..................... C40B 10/00
2015/0159174 A1 6/2015 Frendewey et al.
2015/0232883 A1 * 8/2015 Dahlman ............. C12N 15/907
435/320.1
2016/0289637 A1 10/2016 Goldberg et al.
2016/0374320 A1 * 12/2016 Alt ......................... C07K 16/00
800/3

FOREIGN PATENT DOCUMENTS

| CA | 2936976 | 7/2015 |
|---|---|---|
| CN | 104160031 | 11/2014 |
| CN | 104640985 | 5/2015 |
| JP | 2012-521211 | 9/2012 |
| JP | 2016-539655 A | 12/2016 |
| WO | WO-2010/109165 | 9/2010 |
| WO | WO-2013/079953 | 6/2013 |
| WO | WO-2015/088643 | 6/2015 |
| WO | WO-2015/138620 | 9/2015 |
| WO | WO-2015/166272 | 11/2015 |

OTHER PUBLICATIONS

Winkler et al (F. Gòdia and M. Fussenegger (Eds.), Animal Cell Technology meets Genomics, 403-409). (Year: 2005).*
Clontech (Tet-One™ Inducible Expression System User Manual) (Year: 2010).*
Cheong et al., "Editing of mouse and human immunoglobulin genes by CRISPR-Cas9 system", Nature Communications, 2016, vol. 7: 10934, pp. 1-10.
Cong et al., "Multiplex Genome Engineering Using CRISPR/Cas Systems," Science, Feb. 15, 2013 (online Jan. 3, 2013), 339(6121):819-823.
Decision of Refusal on JP Patent Application No. 2019-502148 dated Nov. 23, 2021 (2 pages) (with English Translation).
Final Office Action on U.S. Appl. No. 16/090,829 dated Feb. 27, 2023 (7 pages).
First Examination Report on IN Patent Application No. 201817035141 dated Aug. 25, 2022 (7 pages).
First Office Action on CN Patent Application No. 201780021643.6 dated Feb. 9, 2022 (19 pages) (with English Translation).
Gu et al., "Independent Control of Immunoglobulin Switch Recombination at Individual Switch Regions Evidenced through Cre-IoxP-Mediated Gene Targeting", Cell, 1993, vol. 73, pp. 1155-1164.
International Preliminary Report on Patentability on PCT PCT/EP2017/056373 dated Oct. 18, 2018 (8 pages).
Maruani et al., "A plug-and-play approach to antibody-based therapeutics via a chemoselective dual click strategy", Nature Communications, 2015, vol. 6: 6645, pp. 1-9.

(Continued)

*Primary Examiner* — Christopher M Gross
(74) *Attorney, Agent, or Firm* — Foley & Lardner LLP

(57) ABSTRACT

According to a first aspect of the invention, a method for the generation of a cell line is provided, comprising the steps of (a) providing a plurality of mammalian B cells, wherein each of the plurality of B cells comprises a transgenic genomic DNA sequence encoding a marker protein inserted into an endogenous immunoglobulin locus comprised in said B cell, and wherein the transgenic genomic DNA sequence is amenable to cleavage by a site directed nuclease, particularly Cas9; (b) replacing the transgenic genomic DNA sequence encoding a marker protein with a second transgenic DNA sequence encoding a protein of interest; (c) sorting B cells based on the presence or absence of the marker protein; and (d) collecting B cells in which the marker protein is absent.

20 Claims, 31 Drawing Sheets

Specification includes a Sequence Listing.

(56) References Cited

OTHER PUBLICATIONS

Non-Final Office Action on U.S. Appl. No. 16/090,829 dated Aug. 26, 2022 (8 pages).
Notice of Objection on IL Patent Application No. 261979 dated Oct. 24, 2021 (no English Translation).
Notice of Reasons for Refusal on JP 2022-037846 dated Feb. 14, 2023 (9 pages) (with English Translation).
Notice of Reasons for Refusal on JP Patent Application No. 2019-502148 dated Apr. 16, 2021 (11 pages) (with English Translation).
Office Action on CA Patent Application No. 3017678 dated Feb. 27, 2023 (4 pages).
Platt et al., "CRISPR-Cas9 Knockin Mice for Genome Editing and Cancer Modeling," Cell, vol. 159, 2014, pp. 440-455, 16 pages.
Preliminary Office Action on BR Patent Application No. BR112018070353.2 dated Aug. 26, 2022 (5 pages) (with Partial English Translation).
Ran et al., "Genome engineering using the CRISPR-Cas9 system", Nature Protocols, 2013, vol. 8(11), pp. 2281-2308.
Second Office Action on CN Patent Application No. 201780021643.6 dated Dec. 27, 2022 (25 pages).

\* cited by examiner

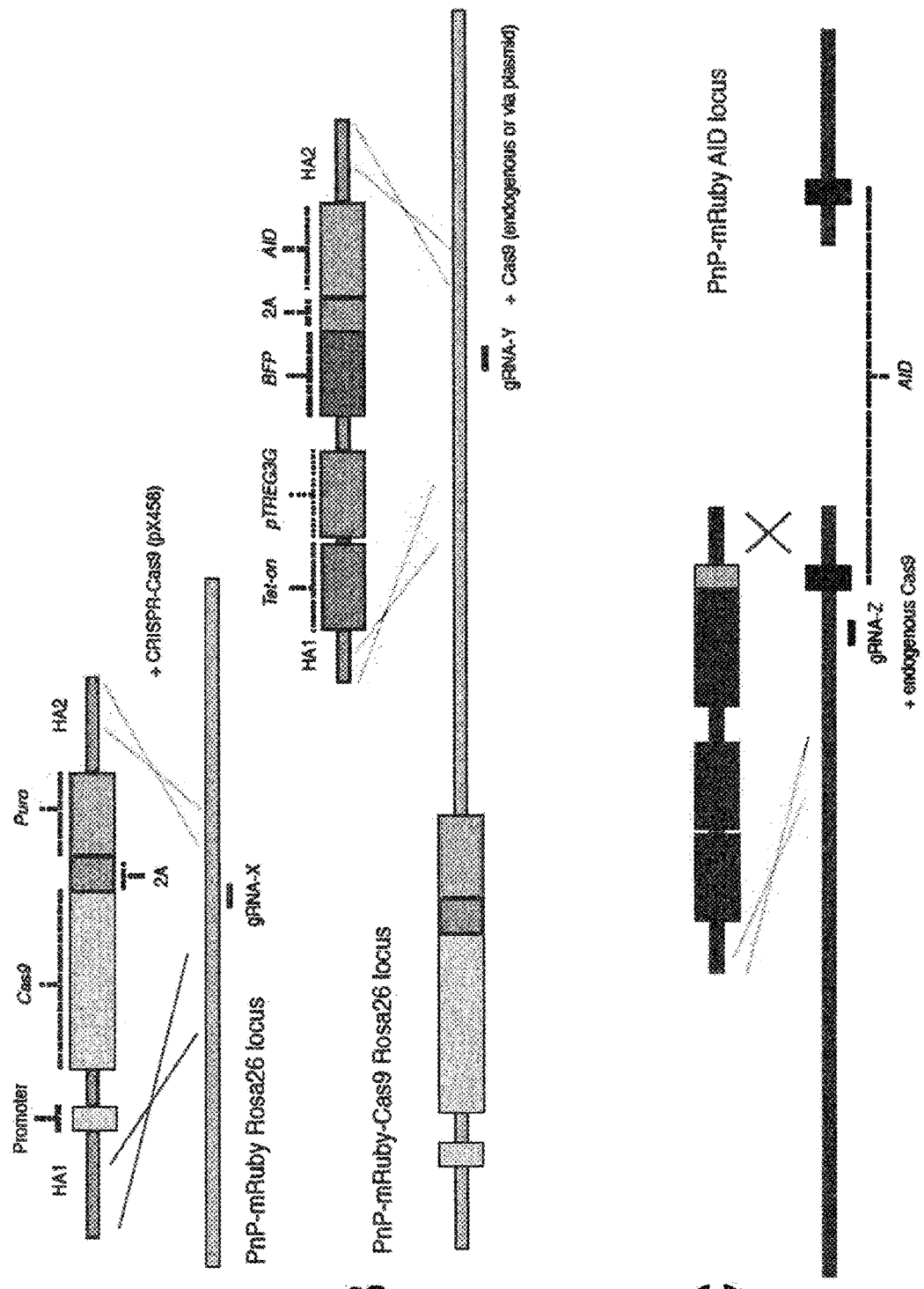

b

E

A

A

A

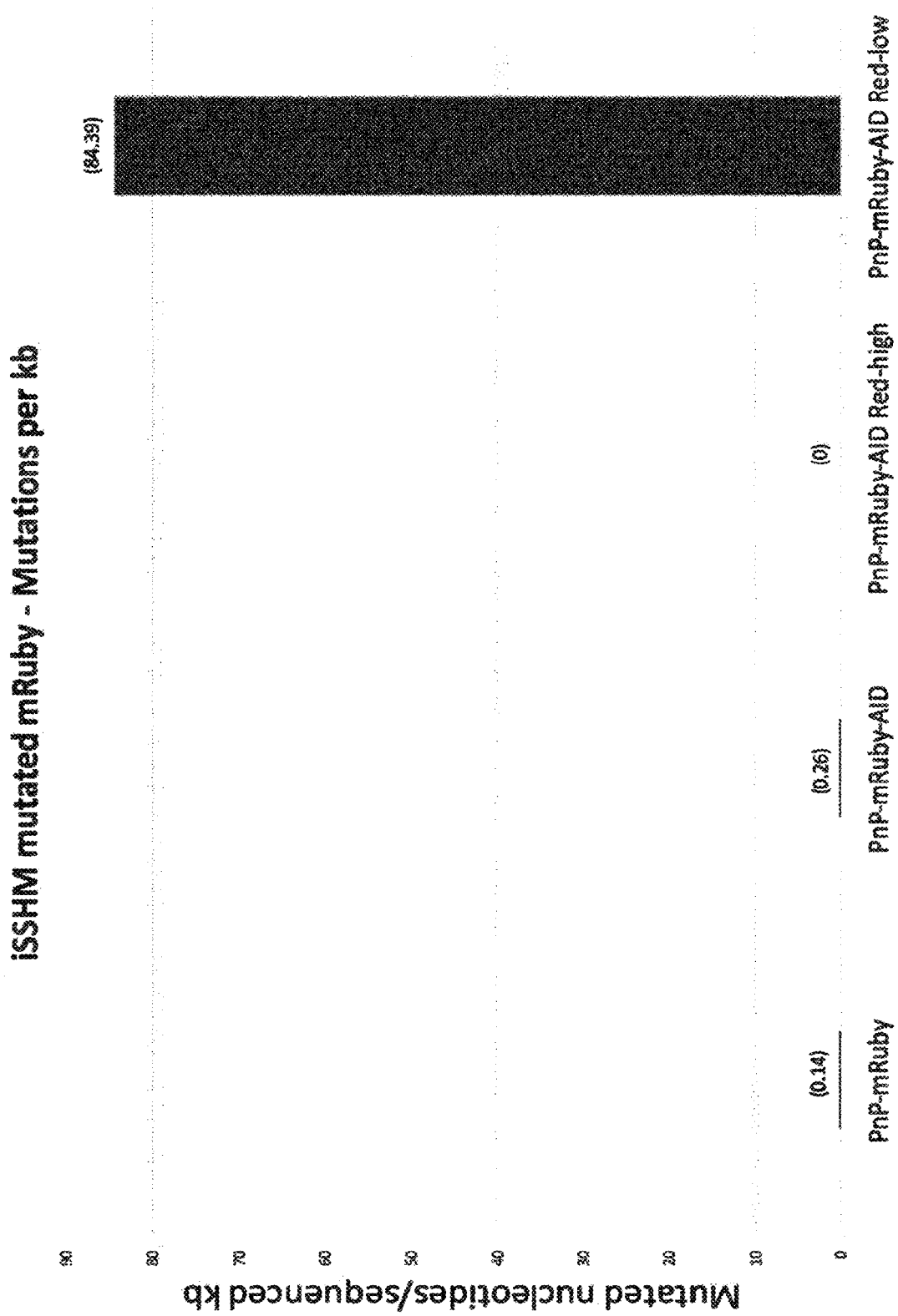

SEQUENCE LISTING

```
Sequence total quantity: 18
SEQ ID NO: 1            moltype = DNA  length = 24
FEATURE                 Location/Qualifiers
misc_feature            1..24
                        note = sequence encodes the targeting sequence of a guide
                        RNA (gRNA) used for gene editing by the CRISPR/Cas system
misc_feature            22..24
                        note = PAM sequence
source                  1..24
                        mol_type = other DNA
                        organism = synthetic construct
SEQUENCE: 1
gctgtcggga gaaagaaatt gtgg                                                24

SEQ ID NO: 2            moltype = DNA  length = 23
FEATURE                 Location/Qualifiers
misc_feature            1..23
                        note = sequence encodes the targeting sequence of a guide
                        RNA (gRNA) used for gene editing by the CRISPR/Cas system
misc_feature            21..23
                        note = PAM sequence
source                  1..23
                        mol_type = other DNA
                        organism = synthetic construct
SEQUENCE: 2
gccctatctc ctcttcagat tgg                                                 23

SEQ ID NO: 3            moltype = DNA  length = 24
FEATURE                 Location/Qualifiers
misc_feature            1..24
                        note = sequence encodes the targeting sequence of a guide
                        RNA (gRNA) used for gene editing by the CRISPR/Cas system
misc_feature            22..24
                        note = PAM sequence
source                  1..24
                        mol_type = other DNA
```

```
                            organism = synthetic construct
SEQUENCE: 3
gttccaatct gaagaggaga tagg                                              24

SEQ ID NO: 4               moltype = DNA  length = 23
FEATURE                    Location/Qualifiers
misc_feature               1..23
                           note = sequence encodes the targeting sequence of a guide
                            RNA (gRNA) used for gene editing by the CRISPR/Cas system
misc_feature               21..23
                           note = PAM sequence
source                     1..23
                           mol_type = other DNA
                           organism = synthetic construct
SEQUENCE: 4
ggagcatgac ggactaatct tgg                                               23

SEQ ID NO: 5               moltype = DNA  length = 23
FEATURE                    Location/Qualifiers
misc_feature               1..23
                           note = sequence encodes the targeting sequence of a guide
                            RNA (gRNA) used for gene editing by the CRISPR/Cas system
misc_feature               21..23
                           note = PAM sequence
source                     1..23
                           mol_type = other DNA
                           organism = synthetic construct
SEQUENCE: 5
gttggtttta gcggagtccc tgg                                               23

SEQ ID NO: 6               moltype = DNA  length = 23
FEATURE                    Location/Qualifiers
misc_feature               1..23
                           note = sequence encodes the targeting sequence of a guide
                            RNA (gRNA) used for gene editing by the CRISPR/Cas system
misc_feature               21..23
                           note = PAM sequence
source                     1..23
                           mol_type = other DNA
                           organism = synthetic construct
SEQUENCE: 6
ggagaagcag gacccatagc agg                                               23

SEQ ID NO: 7               moltype = DNA  length = 23
FEATURE                    Location/Qualifiers
misc_feature               1..23
                           note = sequence encodes the targeting sequence of a guide
                            RNA (gRNA) used for gene editing by the CRISPR/Cas system
misc_feature               21..23
                           note = PAM sequence
source                     1..23
                           mol_type = other DNA
                           organism = synthetic construct
SEQUENCE: 7
ggctatgggt cctgcttctc tgg                                               23

SEQ ID NO: 8               moltype = DNA  length = 23
FEATURE                    Location/Qualifiers
misc_feature               1..23
                           note = sequence encodes the targeting sequence of a guide
                            RNA (gRNA) used for gene editing by the CRISPR/Cas system
misc_feature               21..23
                           note = PAM sequence
source                     1..23
                           mol_type = other DNA
                           organism = synthetic construct
SEQUENCE: 8
gggatcttct attgatgcac agg                                               23

SEQ ID NO: 9               moltype = DNA  length = 23
FEATURE                    Location/Qualifiers
misc_feature               1..23
                           note = sequence encodes the targeting sequence of a guide
                            RNA (gRNA) used for gene editing by the CRISPR/Cas system
misc_feature               21..23
                           note = PAM sequence
source                     1..23
                           mol_type = other DNA
                           organism = synthetic construct
```

```
SEQUENCE: 9
gtggctaaat gagccattcc tgg                                                    23

SEQ ID NO: 10           moltype = DNA  length = 23
FEATURE                 Location/Qualifiers
misc_feature            1..23
                        note = sequence encodes the targeting sequence of a guide
                         RNA (gRNA) used for gene editing by the CRISPR/Cas system
misc_feature            21..23
                        note = PAM sequence
source                  1..23
                        mol_type = other DNA
                        organism = synthetic construct
SEQUENCE: 10
gtcatggaag gttcggtcaa cgg                                                    23

SEQ ID NO: 11           moltype = DNA  length = 23
FEATURE                 Location/Qualifiers
misc_feature            1..23
                        note = sequence encodes the targeting sequence of a guide
                         RNA (gRNA) used for gene editing by the CRISPR/Cas system
misc_feature            21..23
                        note = PAM sequence
source                  1..23
                        mol_type = other DNA
                        organism = synthetic construct
SEQUENCE: 11
gcatgccgtt gatcaccgcc tgg                                                    23

SEQ ID NO: 12           moltype = DNA  length = 24
FEATURE                 Location/Qualifiers
misc_feature            1..24
                        note = sequence encodes the targeting sequence of a guide
                         RNA (gRNA) used for gene editing by the CRISPR/Cas system
misc_feature            22..24
                        note = PAM sequence
source                  1..24
                        mol_type = other DNA
                        organism = synthetic construct
SEQUENCE: 12
gagacctcca tcgcgcactc cggg                                                   24

SEQ ID NO: 13           moltype = DNA  length = 24
FEATURE                 Location/Qualifiers
misc_feature            1..24
                        note = sequence encodes the targeting sequence of a guide
                         RNA (gRNA) used for gene editing by the CRISPR/Cas system
misc_feature            22..24
                        note = PAM sequence
source                  1..24
                        mol_type = other DNA
                        organism = synthetic construct
SEQUENCE: 13
gcagacctcc atcgcgcact ccgg                                                   24

SEQ ID NO: 14           moltype = DNA  length = 24
FEATURE                 Location/Qualifiers
misc_feature            1..24
                        note = sequence encodes the targeting sequence of a guide
                         RNA (gRNA) used for gene editing by the CRISPR/Cas system
misc_feature            22..24
                        note = PAM sequence
source                  1..24
                        mol_type = other DNA
                        organism = synthetic construct
SEQUENCE: 14
gcctcgatgg aaaatactcc gagg                                                   24

SEQ ID NO: 15           moltype = DNA  length = 24
FEATURE                 Location/Qualifiers
misc_feature            1..24
                        note = sequence encodes the targeting sequence of a guide
                         RNA (gRNA) used for gene editing by the CRISPR/Cas system
misc_feature            22..24
                        note = PAM sequence
source                  1..24
                        mol_type = other DNA
                        organism = synthetic construct
SEQUENCE: 15
```

```
                                            -continued
gcgatggaaa atactccgag gcgg                                              24

SEQ ID NO: 16          moltype = DNA  length = 23
FEATURE                Location/Qualifiers
source                 1..23
                       mol_type = other DNA
                       organism = synthetic construct
SEQUENCE: 16
aagcatgtat tgctttacgt ggg                                               23

SEQ ID NO: 17          moltype = DNA  length = 23
FEATURE                Location/Qualifiers
source                 1..23
                       mol_type = other DNA
                       organism = synthetic construct
SEQUENCE: 17
tgcgcgcgtg atagcagcgg cgg                                               23

SEQ ID NO: 18          moltype = DNA  length = 23
FEATURE                Location/Qualifiers
source                 1..23
                       mol_type = other DNA
                       organism = synthetic construct
SEQUENCE: 18
attgcgcgcg tgatagcagg cgg                                               23
```

MAMMALIAN CELL LINE FOR PROTEIN PRODUCTION AND LIBRARY GENERATION

CROSS-REFERENCE TO RELATED APPLICATIONS

This application is a continuation of U.S. patent application Ser. No. 16/090,829, filed Oct. 3, 2018, now pending, which is a U.S. National phase application under 35 U.S.C. § 371 of International Patent Application No. PCT/EP2017/056373, filed Mar. 17, 2017, which claims the benefit of priority under 35 U.S.C. § 119 (e) of European Patent Application No. 16163734.3, filed Apr. 4, 2016, the entire content of each of which is incorporated herein by reference.

SEQUENCE LISTING

The instant application contains a Sequence Listing, which has been submitted electronically in XML file format and is hereby incorporated by reference in its entirety. Said XML copy, created on May 24, 2023, is named 122043-0135 SL.xml and is 29,481 bytes in size.

FIELD OF THE INVENTION

The invention relates to an engineered cell line and to its use for rapid generation of stable cells for protein expression and generation of protein libraries for directed evolution and protein engineering.

BACKGROUND

Currently available methods for protein production from mammalian cells rely primarily on random transgene integration in three cell lines: Human embryonic kidney 293 (HEK293) cells, mouse myeloma cells (Sp20 and NS0), and Chinese hamster ovary (CHO) cells. These methods are both expensive and time consuming. The biotechnology industry standard for therapeutic protein production requires the generation of stable recombinant protein producing cell lines, capable of producing protein near indefinitely, when renewed from frozen cell stocks.

Engineering proteins by directed evolution requires the generation of DNA libraries by in vitro mutagenesis methods (e.g. error prone PCR, degenerate primer PCR mutagenesis, DNA shuffling), followed by cloning into expression hosts and high-throughput screening. The size of libraries that can be generated in mammalian cells is limited due to poor transfection efficiencies. Therefore, high-throughput screening of protein libraries often employs orthogonal surface display platforms, largely based on in vitro or microbial expression (e.g. ribosome, phage, yeast and bacterial display). Compared to mammalian cells, these hosts can have a large impact on protein folding, glycosylation patterns, and expression. Critically though, the standard systems are unable to express and screen some complex proteins effectively (e.g. full-length antibodies). Additionally, in the case of therapeutic proteins, following library screening in in vitro or microbial systems, there is often the need for genetic sub-cloning into mammalian expression systems for proper characterization.

The problem underlying the present invention is to provide a fast, reliable and inexpensive method for the generation of stable mammalian cell lines that can be used for recombinant protein expression and for the generation and screening of large protein libraries for protein engineering and directed evolution applications. This problem is solved by the subject matter of the independent claims.

Definitions

In the context of the present specifications the terms sequence identity and percentage of sequence identity refer to the values determined by comparing two aligned sequences. Methods for alignment of sequences for comparison are well-known in the art. Alignment of sequences for comparison may be conducted by the local homology algorithm of Smith and Waterman, Adv. Appl. Math. 2:482 (1981), by the global alignment algorithm of Needleman and Wunsch, J. Mol. Biol. 48:443 (1970), by the search for similarity method of Pearson and Lipman, Proc. Nat. Acad. Sci. 85:2444 (1988) or by computerized implementations of these algorithms, including, but not limited to: CLUSTAL, GAP, BESTFIT, BLAST, FASTA and TFASTA. Software for performing BLAST analyses is publicly available, e.g., through the National Center for Biotechnology-Information (http://blast.ncbi.nlm.nih.gov/).

One example for comparison of amino acid sequences is the BLASTP algorithm that uses the default settings: Expect threshold: 10; Word size: 3; Max matches in a query range: 0; Matrix: BLOSUM62; Gap Costs: Existence 11, Extension 1; Compositional adjustments: Conditional compositional score matrix adjustment. One such example for comparison of nucleic acid sequences is the BLASTN algorithm that uses the default settings: Expect threshold: 10; Word size: 28; Max matches in a query range: 0; Match/Mismatch Scores: 1.-2; Gap costs: Linear. Unless otherwise stated, sequence identity values provided herein refer to the value obtained using the BLAST suite of programs (Altschul et al., J. Mol. Biol. 215:403-410 (1990)) using the above identified default parameters for protein and nucleic acid comparison, respectively.

In the context of the present specification, the term "B cell" refers to a cell of lymphoid lineage that has completed genomic rearrangement of the immunoglobulin heavy chain and light chain gene loci by V(D)J recombination.

In the context of the present specification, the term "IgH locus" refers to the immunoglobulin heavy chain gene locus.

In the context of the present specification, the term "site-directed endonuclease" refers to an endonuclease selected from the group comprising a CRISPR-associated endonuclease, a zinc finger nuclease (ZFN), a transcription activator-like effector-based nuclease (TALEN) and a meganuclease.

In the context of the present specification, the term "CRISPR-associated endonuclease (Cas9)" refers to the Cas9 endonuclease of Streptococcus pyogenes (SpyCas9), to orthologues of SpyCas9 or to engineered protein variants of SpyCas9 or its orthologues.

In the context of the present specification, the term "orthologue" refers to a gene and its corresponding polypeptide that evolved by vertical descent from a single ancestral gene. In other words, orthologues genes/polypeptides share a common ancestor and were divided when a species diverged into two separate species. The copies of a single gene in the two resulting species are then referred to as orthologues. To ascertain that two genes are orthologues a person skilled in the art can carry out a phylogenetic analysis of the gene lineage by comparing the aligned nucleotide or amino acid sequences of genes or polypeptides.

In the context of the present specification, the term antibody is used in its meaning known in the art of cell biology and immunology; it refers to whole antibodies including but not limited to immunoglobulin type G (IgG), type A (IgA), type D (IgD), type E (IgE) or type M (IgM), any antigen binding fragment or single chains thereof and related or derived constructs. A whole antibody is a glycoprotein comprising at least two heavy (H) chains and two light (L) chains inter-connected by disulfide bonds. Each heavy chain is comprised of a heavy chain variable region ($V_H$) and a heavy chain constant region ($C_H$). The heavy chain constant region is comprised of three domains, $C_H1$, $C_H2$ and $C_H3$. Each light chain is comprised of a light chain variable region (abbreviated herein as $V_L$) and a light chain constant region ($C_L$). The light chain constant region is comprised of one domain, $C_L$. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system.

The term antibody-like molecule in the context of the present specification refers to a molecule capable of specific binding to another molecule or target with high affinity/a Kd≤10E-8 mol/l. An antibody-like molecule binds to its target similarly to the specific binding of an antibody. The term antibody-like molecule encompasses a repeat protein, such as a designed ankyrin repeat protein (Molecular Partners, Züurich), a polypeptide derived from armadillo repeat proteins, a polypeptide derived from leucine-rich repeat proteins and a polypeptide derived from tetratricopeptide repeat proteins.

The term antibody-like molecule further encompasses a polypeptide derived from protein A domains (a protein A domain derived polypeptide), a polypeptide derived from fibronectin domain FN3, a polypeptide derived from consensus fibronectin domains, a polypeptide derived from lipocalins, a polypeptide derived from Zinc fingers, a polypeptide derived from Src homology domain 2 (SH2), a polypeptide derived from Src homology domain 3 (SH3), a polypeptide derived from PDZ domains, a polypeptide derived from gamma-crystallin, a polypeptide derived from ubiquitin, a polypeptide derived from a cysteine knot polypeptide and a polypeptide derived from a knottin.

The term protein A domains derived polypeptide refers to a molecule that is a derivative of protein A and is capable of specifically binding the Fc region and the Fab region of immunoglobulins.

The term armadillo repeat protein refers to a polypeptide comprising at least one armadillo repeat, wherein a armadillo repeat is characterized by a pair of alpha helices that form a hairpin structure.

The term humanized camelid antibody in the context of the present specification refers to an antibody consisting of only the heavy chain or the variable domain of the heavy chain (VHH domain) and whose amino acid sequence has been modified to increase their similarity to antibodies naturally produced in humans and, thus show a reduced immunogenicity when administered to a human being.

A general strategy to humanize camelid antibodies is shown in Vincke et al. "General strategy to humanize a camelid single-domain antibody and identification of a universal humanized nanobody scaffold", J Biol Chem. 2009 Jan. 30; 284(5):3273-3284, and US2011165621A1.

In the context of the present specification, the term fragment crystallizable (Fc) region is used in its meaning known in the art of cell biology and immunology; it refers to a fraction of an antibody comprising two identical heavy chain fragments comprised of a $C_H2$ and a $C_H3$ domain, covalently linked by disulfide bonds.

Further definitions of terms used herein are given throughout the document where appropriate.

DESCRIPTION OF THE INVENTION

According to a first aspect of the invention, a method for the generation of a cell line is provided, comprising the steps of
  a. providing a plurality of mammalian B cells, wherein each of the plurality of B cells comprises a transgenic genomic DNA sequence encoding a marker protein, wherein the transgenic genomic DNA sequence is inserted into an endogenous immunoglobulin locus comprised in said B cell, particularly an IgH locus, and wherein said transgenic genomic DNA sequence is amenable to cleavage by a site-directed nuclease, particularly CRISPR-associated endonuclease (Cas9);
  b. replacing said transgenic genomic DNA sequence encoding said marker protein with a second transgenic DNA sequence encoding a protein of interest;
  c. sorting said B cells based on the presence or absence of said marker protein; and
  d. collecting B cells in which said marker protein is absent.

In certain embodiments, the marker protein is a fluorescent protein. In certain embodiments, the marker protein is a protein conferring resistance to an antibiotic drug.

In certain embodiments, said marker protein is a fluorescent protein and said sorting is done by flow cytometry.

In the context of the present specification, the expression "replacing said transgenic genomic DNA sequence encoding said marker protein with a second transgenic DNA sequence encoding a protein of interest" relates to both actual replacement of the DNA sequence and functional replacement, in the way that the marker protein is no longer expressed and the protein of interest is expressed instead.

The skilled person is aware that the expression "said transgenic genomic DNA sequence [encoding a marker protein] is amenable to cleavage by a site directed nuclease" comprises both cleavage within the DNA sequence encoding the marker protein and cleavage within the immediate 3' and/or 5' flanking regions.

In certain embodiments, said transgenic genomic sequence is flanked by a 5' flanking sequence tract and a 3' flanking sequence tract, wherein said 5' flanking sequence tract and/or said 3' flanking sequence tract is amenable to cleavage by a site directed nuclease.

In certain embodiments, said flanking sequence tracts comprise 0 to 1500 nucleotides, particularly 0 nucleotides or 1 to 700 nucleotides, more particularly 0 nucleotides or 1 to 100 nucleotides.

The sites amenable to cleavage by the site-directed nuclease, particularly Cas9, are typically within 500 nucleotides of the sequence encoding the marker protein or within the sequence encoding the marker protein.

In certain embodiments, the protein of interest is an antibody, an antibody-like molecule, a humanized camelide antibody or an immunoglobulin antigen-binding fragment.

In those instances where the later inserted gene of interest is an antibody, the endogenous immunoglobulin $V_H$ gene is replaced or disrupted by the transgenic genomic DNA sequence encoding a marker protein.

In the context of the present specification, the term "$V_H$ gene" refers to the DNA sequence encoding the variable region of an immunoglobulin heavy chain.

In the context of the present specification, the term "$V_L$ gene" refers to the DNA sequence encoding the variable region of an immunoglobulin light chain.

In certain embodiments, the plurality of B cells is selected from the group comprising primary B cells, immortalized B cells, hybridoma cells, myeloma cells, plasmacytoma cells, and lymphoma cells.

In certain embodiments, the marker protein and/or the protein of interest is expressed under control of an endogenous immunoglobulin promoter, particularly the $V_H$ promoter.

In the context of the present specification, the term "$V_H$ promoter" refers to the promoter of the "$V_H$ gene".

In certain embodiments, the endogenous $V_H$ gene and the endogenous $V_L$ gene are disrupted in each of said plurality of B cells. This means that the B cells can neither express an immunoglobulin heavy chain nor an immunoglobulin light chain.

In certain embodiments, the plurality of B cells is genetically modified to constitutively express said CRISPR-associated endonuclease.

In certain embodiments, the plurality of B cells is genetically modified to express an activation-induced cytidine deaminase (AID) in an inducible and titratable manner.

In the context of the present specification, the term "activation-induced cytidine deaminase" refers to an enzyme able to deaminate cytosine bases within genomic DNA, turning them into uracil (EC 3.5.4.38).

In certain embodiments, the plurality of B cells comprises a safe harbor locus, and a first expression cassette comprising a DNA sequence encoding the CRISPR-associated endonuclease is inserted into said safe harbor locus.

In the context of the present specification, the term "safe harbor locus" refers to a chromosomal location amenable for integration of transgenes. Transgenes integrated in a safe harbor locus are stably expressed and do not perturb endogenous gene activity. Examples of safe harbor loci are the murine Rosa26 locus or the AAVS1 locus.

In certain embodiments, the CRISPR-associated endonuclease inserted into said safe harbor locus is under the control of a constitutively active promoter, particularly the CAG promoter, CBh promoter, or the CMV promoter.

The CAG promotor is a hybrid construct consisting of the cytomegalovirus enhancer fused to the chicken beta-actin promoter (Jun-ichi et al., Gene 79(2):269-277). CBh promoter is a hybrid form of the CBA (chicken beta-actin) promoter (Gray et al., Hum Gene Ther., 2011, 22(9):1143-1153). The term "CMV promoter" refers to the human cytomegalovirus immediate early enhancer and promoter sequence of a human herpesvirus such as human herpesvirus 5 strain Toledo (GenBank GU937742.2). Exemplary CMV sequences are deposited in GenBank under the references X03922.1, M64940.1, M64941.1, M64942.1, M64943.1, M64944.1 and K03104.1.

In certain embodiments, the plurality of B cells comprises a safe harbor locus, and a second expression cassette comprising a DNA sequence encoding said activation-induced cytidine deaminase (AID) is inserted into said safe harbor locus.

In certain embodiments, the second expression cassette comprises regulatory sequences amenable to inducible activation by an activator molecule.

In certain embodiments, the second expression cassette comprises an inducible expression system, particularly the Tet-One inducible expression system. The Tet-One inducible expression system comprises a transactivator protein (Tet-On) and an inducible promotor ($P_{TRE3GS}$) In the presence of the antibiotic doxycycline, Tet-On binds to tetO sequences in $P_{TRE3GS}$ and activates a high level of transcription of the gene downstream of the promoter, i.e. of the gene encoding activation-induced cytidine deaminase (AID). If doxycyclin concentration is reduced, expression is reduced, thus generating a titratable system of AID expression and somatic hypermutation.

In the context of the present specification, the term "somatic hypermutation (SHM)" refers to a cellular mechanism by which multiple genomic mutations are generated. SHM involves the deamination of cytosine to uracil in DNA by the enzyme activation-induced cytidine deaminase (AID). The resulting basepair mismatch (uracil-guanosine, U:G) can bring about a genomic mutation, e.g. via excision of the uracil base and filling of the gap by an error-prone DNA polymerase, or via DNA replication during which the uracil is treated as a thymidine.

In the context of the present specification, the term "inducible synthetic somatic hypermutation (iSSHM)" refers to SHM that can be induced in said plurality of B cells by activation of AID expression from an inducible expression system.

In certain embodiments, said replacing of said transgenic genomic DNA sequence is mediated by Cas9-mediated site-directed DNA cleavage and subsequent integration of said second transgenic DNA sequence by homology directed repair (HDR) or non-homologous end joining (NHEJ). This method comprises providing a guide RNA and a replacement DNA.

In the context of the present specification, a guide RNA or gRNA is a short synthetic RNA composed of a sequence necessary for Cas9-binding and a user-defined "targeting sequence" of approximately 23 nucleotides which defines the genomic target to be modified (see table 2).

Such guide RNAs can be provided by the transfection of in vitro transcribed RNA or commercially synthesized oligonucleotide RNA. Alternatively, the guide RNA can be provided by transfection or viral transduction of a DNA sequence into the cell, wherein such DNA sequence encodes (and expresses in the cell) the guide RNA. Multiple guide RNAs can be provided for simultaneous cleavage of multiple genomic sites in the IgH locus (this improves efficiency of transgene insertion).

The replacement DNA comprises said second transgenic DNA sequence encoding a protein of interest. Replacement DNA can be provided by transfection or viral transduction of either circular or linear double-stranded DNA (dsDNA) or single-stranded DNA (ssDNA) (e.g., oligonucleotides).

In certain embodiments of this aspect of the invention, said protein of interest is a full-length antibody. The full-length antibody can be based on a synthetic antigen binding fragment (sFAb) construct. To reintroduce a new full-length antibody, while avoiding targeting of both the immunoglobulin heavy chain locus and the immunoglobulin light chain locus, both full-length light and heavy chains can be expressed from the native $V_H$ promoter as a single transcript (FIG. 2B).

In certain embodiments, the plurality of B cells are mouse hybridoma cells.

In certain embodiments, the plurality of B cells are mouse hybridoma cells and the murine $C_H$ region is replaced with a $C_H$ region of a different species, particularly with a human $C_H$ region. This allows the generation of a human antibody by a mouse hybridoma cell.

In the context of the present specification, the term "$C_H$ region" refers to the DNA sequence encoding the constant region of an immunoglobulin heavy chain.

In certain embodiments of this aspect of the invention, said second transgenic nucleic acid sequence comprises more than one gene of interest and additional promoters. This way, a cell line that stably expresses multiple genes or an entire synthetic genetic network can be generated by the inventive method.

Current state of the art methods for recombinant protein expression from stable mammalian cells take at least 8-10 weeks to develop, with commercial entities charging upwards of 10,000 USD per protein. The generation of stable cell lines for industrial therapeutic purposes takes up to one year.

Usually, analysis of multiple clones is required, due to varying efficiency of protein production. Factors affecting clonal productivity are number of integrations and integration site, as gene silencing is known to occur over time at some integration sites.

According to a second aspect of the invention, a method for the generation of a library of protein variants is provided. This method comprises a method according to the first aspect of the invention or any of its embodiments mentioned above, followed by the additional step of modifying regions of the transgenic DNA with randomized nucleic acid sequences (through randomized regions on donor dsDNA or ssDNA). Thus, genomic mutations within the protein of interest by site-directed mutagenesis are generated.

According to an alternative of this aspect of the invention, a method for the generation of a library of protein variants comprises the method according to the first aspect of the invention or any of its embodiments mentioned above, followed by the additional step(s) of
   a. inducing expression of activation-induced cytidine deaminase (AID), thus generating multiple genomic mutations within the protein of interest by inducible synthetic somatic hypermutation (iSSHM), or
   b. modifying regions of said transgenic DNA with randomized nucleic acid sequences, thus generating genomic mutations within the protein of interest by site-directed mutagenesis.

According to a third aspect of the invention, a method for the generation of a library of protein variants is provided. The method comprises the method according to the first aspect of the invention, followed by the additional step(s) of inducing expression of activation-induced cytidine deaminase (AID), thus generating multiple genomic mutations within the protein of interest by inducible synthetic somatic hypermutation (iSSHM).

AID is especially efficient in generating mutations within the immunoglobulin (IgH or IgK or IgL) locus. It is therefore advantageous for the iSSHM that the DNA sequence encoding the protein of interest is inserted into the immunoglobulin locus, such as the IgH locus.

In certain embodiments, said modifying of said regions of the transgenic genomic DNA sequence is mediated by Cas9-mediated site-directed DNA cleavage and either
   a. subsequent integration of said randomized transgenic DNA sequences by homology directed repair (HDR) or non-homologous end joining (NHEJ), or
   b. subsequent insertion or deletion of nucleotides through the repair of the transgenic DNA sequence by NHEJ.

This method comprises providing a guide RNA and replacement DNA in an analogous manner to the first aspect of the invention. Guide RNA and randomized nucleic acid sequences can be provided by the transfection or viral transduction of dsDNA or ssDNA, comprising degenerate nucleotides or trinucleotide codons. To improve the HDR efficiency of ssDNA, phosphorothioate bonds are introduced at the 5' and 3' ends, as well as throughout the ssDNA oligonucleotide. Phosphorothioate bonds are an exchange of the non-bridging oxygen of the phosphate backbone with a sulfur atom. The sulfur atom in the phosphate backbone increases the ssDNA's resistance to nuclease degradation.

In the context of the present specification, the term "degenerate nucleotide" refers to the position of a DNA sequence encoding any mixed nucleotide composition.

In the context of the present specification, the term "trinucleotide", or trimer phosphoramidite, refers to three contiguous nucleotides of a DNA sequence encoding any mixed amino acid composition.

The skilled person is aware that the generation of a library of protein variants according to the second aspect of the invention comprises the generation of a library of cell lines.

In those instances, where the protein of interest is an antibody, the mutated antibodies are screened for improved or novel antigen binding. Fluorescently labelled antigen is added to the cells and the cells are screened by FACS. Alternatively, an initial screening step can be carried out by magnetic-associated cell sorting (MACS) using magnetic beads conjugated to antigen.

Several rounds of screening and iSSHM or site-directed mutagenesis can be performed to continue the engineering of an antibody or protein.

In certain embodiments, the marker protein is a fluorescent protein.

By way of non-limiting example, such fluorescent protein may be selected from green fluorescent protein (GFP) from *Aequorea victoria* and derivatives thereof, such as
   enhanced blue fluorescent protein (EBFP), enhanced blue fluorescent protein 2 (EBFP2), azurite, mKalama1, sirius
   enhanced green fluorescent protein (EGFP), emerald, superfolder avGFP, T-sapphire
   yellow fluorescent protein (YFP), enhanced yellow fluorescent protein (EYFP), citrine, venus, YPet, topaz, SYFP, mAmetrine
   enhanced cyan fluorescent protein (ECFP), mTurquoise, mTurquoise2, cerulean. CyPet, SCFP.

A fluorescent protein for practicing the invention may also be selected from the group comprising fluorescent protein from *Discosoma striata* and derivatives thereof:
   mTagBFP,
   TagCFP, AmCyan, Midoriishi Cyan, mTFP1
   Azami Green, mWasabi, ZsGreen, TagGFP, TagGFP2, TurboGFP, CopCFP, AceGFP
   TagYFP, TurboYFP, ZsYellow, PhiYfP
   Kusabira Orange, Kusabira Orange2, mOrange, mOrange2, dTomato, dTomato-Tandem, DsRed, DsRed2, DsRed-Express (T1), DsRed-Express2, DsRed-Max, DsRed-Monomer, TurboRFP, TagRFP, TagRFP-T
   mRuby, mApple, mStrawberry, AsRed2, mRFP1, JRed, mCherry, eqFP611, tdRFP611, HcRed1, mRaspberry
   tdRFP639, mKate, mKate2, katushka, tdKatushka, HcRed-Tandem, mPlum, AQ143.

Fluorescent proteins also comprise proteins derived from alpha-allophycocyanin from the cyanobacterium *Trichodesmium erythraeum* such as small ultra red fluorescent protein (smURFP).

The skilled person is aware that the method according to the first aspect of the invention may also work with other fluorescent proteins not included in the list above.

Another aspect of the invention provides a human B cell line comprising an expressed transgenic genomic DNA sequence inserted into an endogenous immunoglobulin locus comprised in said B cell obtained by a method according to the first, second or third aspect of the invention.

According to yet another aspect of the invention, a protein obtained by a method according to the first, second or third aspect of the invention is provided.

According to yet another aspect of the invention, a library of protein variants obtained by the method according to the second or third aspect of the invention is provided.

According to yet another aspect of the invention, a mammalian B cell is provided, wherein
 a. a transgenic genomic DNA sequence encoding a marker protein is inserted into an endogenous immunoglobulin locus comprised in said B cell, particularly an IgH locus, wherein the marker gene encodes a fluorescent protein, and wherein
 b. said transgenic genomic sequence is amenable to cleavage by a site directed nuclease, particularly CRISPR-associated endonuclease (Cas9).

In certain embodiments of this aspect of the invention, the endogenous $V_H$ gene and the endogenous $V_L$ gene of said B cell are disrupted.

In certain embodiments, the mammalian B cell is a human cell.

Yet another aspect of the invention relates to a plurality of mammalian B cells, each of which encodes a variant of a transgene protein. The plurality in its entirety constitutes a library of such variants. Each member of the plurality of B cells contained in the plurality comprises a transgenic genomic DNA sequence encoding a variant of a protein or interest. The transgenic genomic DNA sequence is inserted into an endogenous immunoglobulin locus comprised in said B cell, particularly an IgH locus, and each variant encoded by a member of said plurality is different from any other variant encoded by another member of said plurality.

The skilled person understands that each member of the plurality is likely to be represented by more than one individual cell, i.e. several cells of a clone may constitute a member. The important aspect here is that the variant is the same for one member, and that a large number (in certain embodiments, equal or more than ≥100, ≥1000, ≥10.000 or even ≥100.000 different variants may be present in the plurality.

In certain embodiments of this aspect of the invention, each variant encoded in the plurality of B cells is different from another variant in one to five positions of its amino acid sequence.

In certain embodiments of this aspect of the invention, each variant is at least 80%, 85%, 90%, 95%, 97%, 98% or 99% identical to any another variant encoded by a member of said plurality. In other words, the variants may share a significant part of their sequence between individual members, and yet represent a very broad spectrum of variants.

In certain embodiments of this aspect of the invention, the plurality of B cells is selected from the group comprising primary B cells, immortalized B cells, hybridoma cells, myeloma cells, plasmacytoma cells, and lymphoma cells.

Wherever alternatives for single separable features are laid out herein as "embodiments", it is to be understood that such alternatives may be combined freely to form discrete embodiments of the invention disclosed herein.

EXAMPLES

The invention is further illustrated by the following examples and figures, from which further embodiments and advantages can be drawn. These examples are meant to illustrate the invention but not to limit its scope.

To realize the invention, the inventors have generated a plug-and-(dis)play (PnP) mammalian cell line. The inventors used mouse B-lymphocytes (hybridoma cells), which function as production factories for antibody proteins. The PnP cell line consists of the following components:

1) The endogenous $V_H$ gene in the IgH locus was replaced with a fluorescent protein (mRuby, originally referred to as mRuby2, originated from the Addgene.org plasmid #: 40260 (Lam et al., Nat Methods 2012, 9:1005-1012)). This was accomplished by transfecting WT hybridoma cells with a CRISPR-Cas9 plasmid (pX458) (Addgene.org plasmid #: 48138) (Cong et al., Science 2013, 339:819-823) with a guide RNA (gRNA) targeting the intron between $V_H$ and IgG CH1 genes. Also co-transfected was a donor DNA construct consisting of the mRuby gene and homology arms corresponding to the IgH locus of WT hybridoma cells. The CRISPR-Cas9 system introduced a targeted double-strand break (DSB) in the DNA of the WT cells, which promoted DNA repair mechanisms of homology directed repair (HDR) or non-homologous end joining (NHEJ) resulting in site specific integration of the mRuby gene in place of the $V_H$ gene. The native IgH promoter is used for expression of mRuby (FIG. 1a-d).

2) The endogenous $V_L$ gene in the IgK locus was deleted to generate a light chain knockout cell line. This was accomplished by transfecting the hybridoma cells (described in 1) with pX458 with gRNAs targeting two sites flanking the $V_L$ gene in the IgK locus. This results in deletion of the $V_L$ gene and knockout of the endogenous light chain expression in hybridoma cells (FIG. 1e-g).

The resulting cells are referred to as PnP-mRuby cells.

3) PnP-mRuby cells were converted into cells that express a new antibody, these are referred to as PnP-IgG cells. This was accomplished by transfecting PnP-mRuby cells with pX458 with gRNA targeting the mRuby gene (now integrated in the IgH locus). Also co-transfected was a donor DNA construct of a synthetic antibody fragment (sFAb) with homology arms corresponding to the IgH locus. Similar to 1), CRISPR-Cas9 promotes a DSB and HDR or NHEJ, which results in targeted integration of the sFAb into the IgH locus. The outcome of this is that full-length antibody (IgK and IgH) is expressed from the IgH locus as a single RNA transcript (FIG. 2)

PnP-mRuby cells can be converted into a stable mammalian cell line expressing recombinant protein (e.g., PnP-IgG) with a single transfection and selection step (FIG. 3, 4).

4) PnP-mRuby cells were engineered for constitutive expression of Cas9 (PnP-mRuby-Cas9 cells). This was accomplished by transfecting PnP-mRuby cells with pX458 with gRNA targeting a site in the safe harbor locus of Rosa26 and a donor DNA construct consisting of Cas9-2A-puromycin, under the control of a constitutively active promoter (e.g. CAG promoter or CMV promoter) (Addgene.org plasmid #48139) (Platt et al., CELL 2014, 159:440-455: Ran et al., Nat Protoc 2013, 8:2281-2308). An advantage of these cells is that they eliminate the need to transfect with CRISPR-Cas9 plasmid (pX458), therefore to convert PnP-mRuby cells to a cell line expressing a recombinant protein (e.g., PnP-IgG) only gRNA (in vitro transcribed or commercially synthesized) and donor construct (replacement DNA, e.g., sFAb) need to be transfected, which improves efficiency (FIG. 5a).

In vitro transcription of gRNAs is performed by using template DNA consisting of a T7 promoter, a customized spacer region encoding the gRNA and the trans-activating region in a manner according to the pX458 design. This construct serves as a template for the MEGAscript® T7 transcription kit (Thermo, AM1334), thus in vitro transcription results in a chimeric single gRNA. The protocol is adapted from: https://www.protocols.io/view/In-vitro-transcription-of-guide-RNAs-d4w8xd?step=3

5) PnP-IgG cells expressing antigen specific antibodies for HEL (PnP-HEL23) were further modified in the complementary determining region 3 of the $V_H$ gene (CDR-H3) to generate a large library of protein variants by site-directed mutagenesis, which can then be screened for increased antigen affinity or novel antigen binding. This was accomplished in the following manner:

The sFAb gene of PnP-HEL23 cells was modified to knock out antibody expression. By transfecting these cells with the pX458 vector containing guide RNA targeting the CDR-H3, antibody expression is knocked out by the insertion or deletion of nucleotides through repair via NHEJ. The insertion or deletion of nucleotides cause frameshift mutations and subsequently alters all downstream amino acids remaining in the gene. Single cell clones negative for antibody expression can be isolated by flow cytometry and expanded. A suitable clone is then selected (PnP-HEL23-IgH⁻) by phenotypic and genotypic characterization. A library of protein variants can then be derived from said cell clone through integration of randomized nucleic acids.

Affinity maturation of the antibody can be accomplished by providing a guide RNA targeting the CDR-H3 and replacement DNA by transfection or viral transduction, wherein the replacement DNA contains a region of three randomized nucleic acids corresponding to a single amino acid at each position found within the original CDR-H3 (FIG. 11).

A protein library for the discovery of novel, antigen specific antibodies may also be generated by complete replacement of the CDR-H3 in an analogous manner to the method described for antibody affinity maturation. Guide RNA targeting the CDR-H3 and replacement DNA are provided by transfection or viral transduction, wherein the replacement DNA contains a region comprising three to 69 randomized nucleic acids corresponding to variable lengths of the CDR-H3. (FIG. 11).

In both instances, cells producing functional antibodies against the target antigen are screened and sorted by flow cytometry.

6) This plug-and-(dis)play (PnP) mammalian cell line was further engineered so that they are able to generate a large library of protein variants by inducible synthetic somatic hypermutation iSSHM, which can then be used for directed evolution and high-throughput screening (PnP-iAID cells). This was accomplished in the following manner:

PnP-mRuby2 cells were transfected with pX458 vector containing sgRNA targeting the safe harbor locus ROSA26 and a donor construct (replacement DNA). The donor construct comprises the Tet-One System (Clontech) (Heinz et al., Human Gene Therapy 2011, 22:166-176), composed of the following components (FIG. 5b):

i. In the forward direction, a human phosphoglycerate kinase 1 (hPGK) promoter that provides constitutive expression of the Tet-On 3G protein;

ii. in the forward direction, coding sequence of Tet-On 3G Transactivator Protein, a fusion protein of rTetR linked to the VP16 activation domain (rtTA);

iii. in the reverse direction, $P_{TRE3GS}$ inducible promoter, a modified version of $P_{TRE3G}$, which consists of a modified tet responsive element (TRE) and contains 7 direct repeats of the tet operator joined to a minimal CMV promoter;

iv. a gene of interest (GOI), whose expression is driven by the $P_{TRE3GS}$ promoter, and which comprises DNA sequences encoding:
  i. a fluorescent reporter protein (e.g., GFP or blue fluorescent protein (BFP));
  ii. a "self-cleaving" 2A peptide;
  iii. activation-induced cytidine deaminase (AID):

v. homology arms (>500 bp) corresponding to the Rosa 26 locus.

Alternatively, a donor construct without homology arms can be used. In these instances, the donor construct can be integrated via NHEJ.

In an alternative approach, PnP-mRuby-Cas9 cells were used as a starting platform for the creation of the PnP-iAID cell line. In this instance, PnP-mRuby-Cas9 cells were transfected with in vitro transcribed gRNA targeting an orthogonal site in the safe harbor locus of Rosa26 and a donor construct (replacement DNA). The donor comprises the same components described above in 4).

In an alternative approach, PnP-mRuby-Cas9 cells were transfected with in vitro transcribed gRNA targeting the native AID genomic locus of mice. In this case the donor construct consisted of the same elements described above in 4) but with exception that in iv) only the first intron of the gene encoding activation-induced cytidine deaminase (AID) is present (FIG. 5c).

In the presence of the antibiotic doxycycline (Dox), Tet-On binds to tetO sequences in $P_{TRE3GS}$ and activates a high level of transcription. However, in the presence of decreasing amounts of Dox, expression is reduced, thus generating a titratable system of AID expression and SHM. PnP-iAID cells can be cultured for long periods of time with Dox in order to generate large libraries of protein variants in the IgH locus. Directed evolution and engineering of proteins can then be accomplished by high-throughput screening via flow cytometry (FIG. 5d).

(B) HDR percentages are estimated by flow cytometric analysis though labeling with a fluorescently tagged antigen. Percentages displayed are cells that had regained antigen specific antibody expression towards HEL. Data presented is representative of n=2 experiments after screening for transfection positive (GFP+) cells. 1: Cas9 plasmid; 2: Cas9 RNP; 3: Cas9 RNP+Modified ssODN: 4: Cas9 Cell+Modified ssODN.

Figure 12:
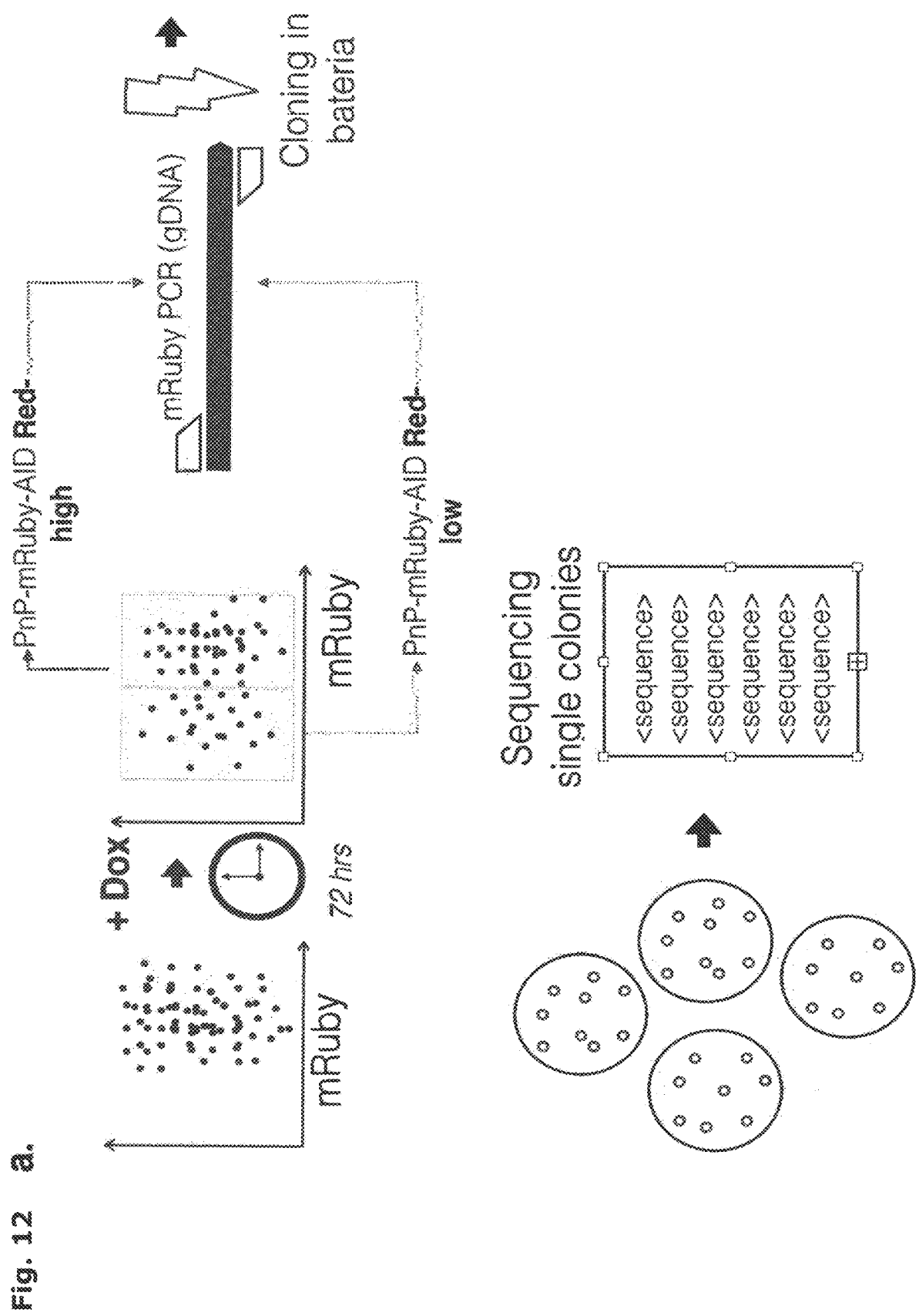
Figure 12:
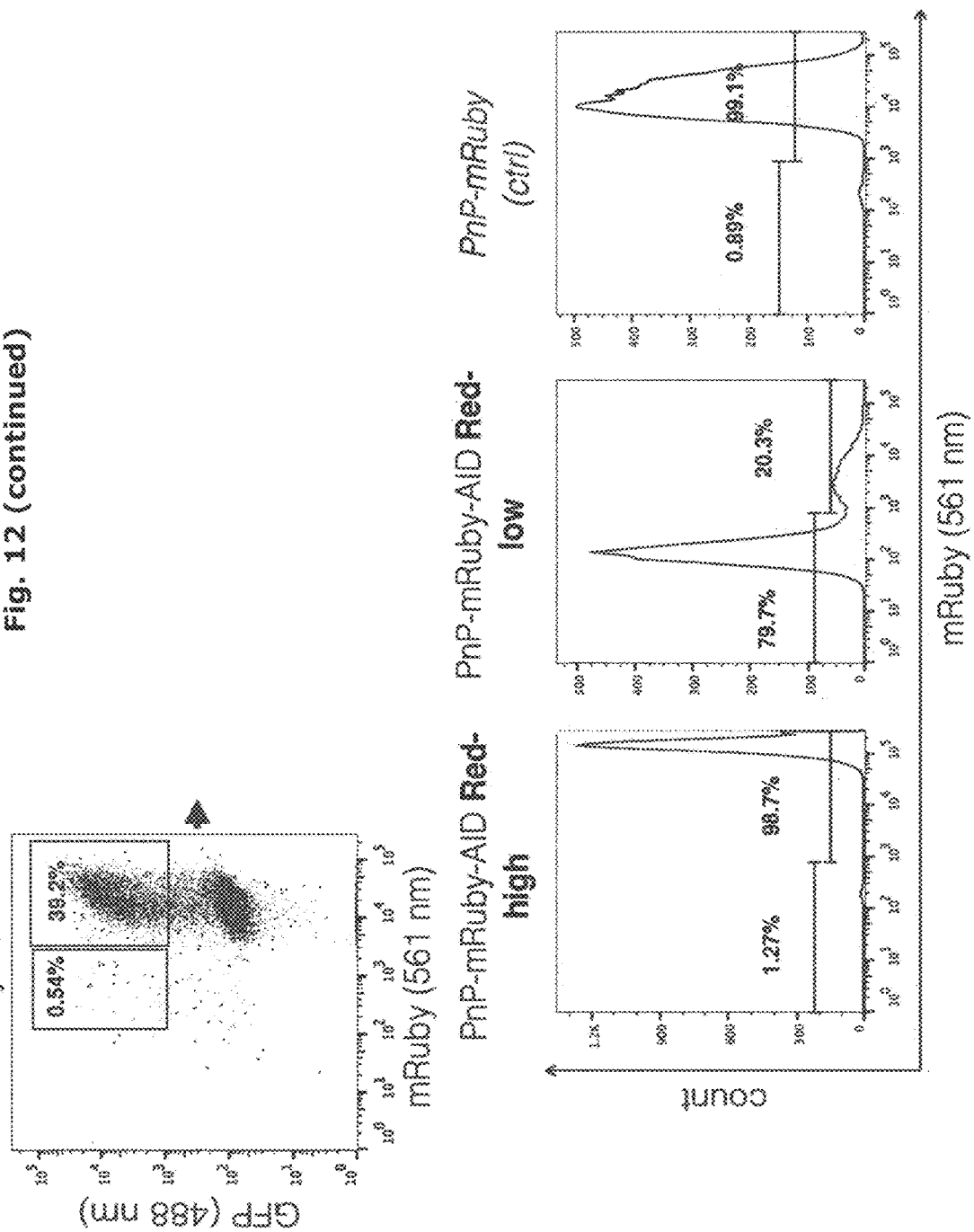
Figure 12:
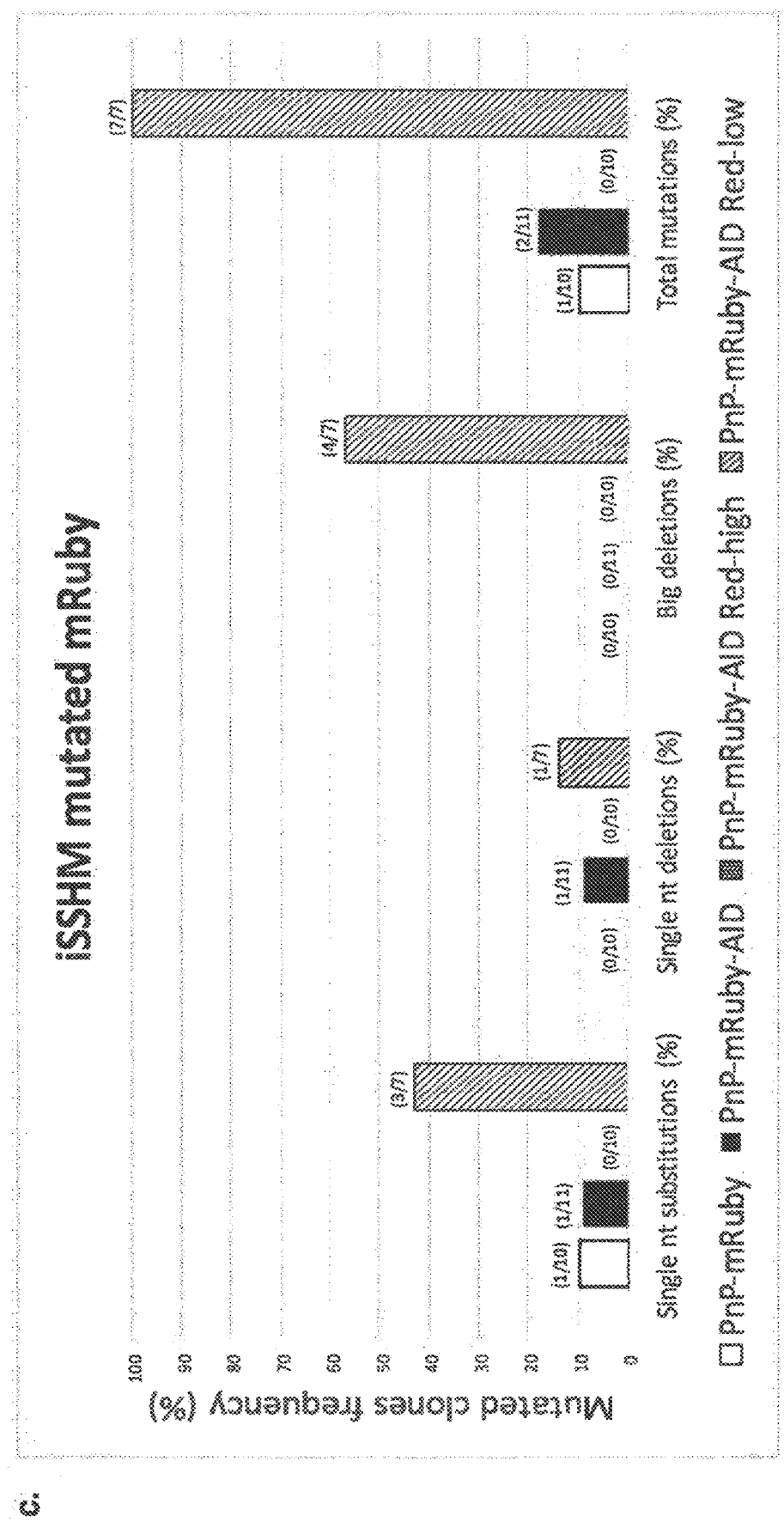

FIG. 12: Evaluation of inducible-AID's mutation activity. (a) Experiment outline. PnP-mRuby cells selected for integrated TetOne-AID (via GFP-2A) were induced by Dox (1 µg/ml, induction renewed daily) for 72 hours and FACS sorted for high (unchanged) or low (decreased) mRuby fluorescence. Genomic DNA (gDNA) was extracted from the two populations and mRuby gene was clone and Sanger sequenced. (b) FACS plots displaying, from left to right: cells at sorting (the displayed gates and percentages are not the original ones, but re-created post-analysis for illustrative purpose); the two sorted populations after recovery: PnP-mRuby-AID Red-high, sorted for high rnRuby expression, and PnP-rnRuby-AID Red-low, sorted for decreased mRuby expression; PnP-mRuby cells used as positive control. Genomic DNA was isolated for sequencing analysis. (c) Sequences were mapped to mRuby and investigated for the presence of mutations. This graph shows the percentage of mutated clones for each sample. By 'big deletions' it is meant anything bigger than 1 nucleotide. The only sample yielding clones with big deletions was PnP-rnRuby-AID Red-low. Values on top of the bar report the actual frequency in the cohort (before % conversion) (d) Mutations per kb in the analysed clones. For each of the four samples/cohorts, the sequenced nucleotides (mRuby ORF only, 711 bp) for all analysed clones were summed, and the frequency of mutated nucleotides per kb was calculated consequentially. Notably, in case of deletions, each missing nucleotide was calculated as a mutated one. Note: the data reported in (c) and (d) does not account for the coding or non-coding (silent) outcome of single nt substitutions.

TABLE 1

Summary of hybridoma clones

| Cell Type | Type | Description |
|---|---|---|
| WT | WEN1.3 | Wen 1.3 cells are derived from a mouse infected with LCMV. They express IgG2c and are specific for LCMV GP-1 antigen. |
| PnP-mRuby | 1E9.C3 | WEN 1.3 cells were transfected with pX458 with gRNA-E and mRuby donor construct and sorted for Cas9 positive expression (2A-GFP). This was followed by a first round of sorting for mRuby-positive cells, followed by a second single cell sort for mRuby. A single cell clone was selected and then transfected with pX458 with gRNA-F and H and sorted for Cas9 positive expression (2A-GFP). Cells were then sorted for IgK negative expression. A second round of single cell sorting was performed followed by genomic PCR to identify a clone with VL deletion. This final clone represents 1E9.C3 |
| PnP-mRuby-pA | D2 | PnP-mRuby-pA cells include a polyadenylation signal following the mRuby gene's stop codon to increase cell fluorescence. PnP-mRuby-pA cells were generated in an identical manner to PnP-mRuby cells, but with a donor construct including the polyadenylation signal. |
| PnP-mRuby-Cas9 | 1AD (winner selection in progress) | Clone D2 was transfected with pX458 with gRNA-P and Cas9-2A-Puro-GFP HDR donor linearized. Cells were sorted for Cas9 positive expression (2A-BFP) and expanded. Cells were sorted for GFP positive expression and expanded. Cells were then cultured in growth medium supplemented with 2.5 ug/ml puromycin for up to one week. Single cells were sorted for GFP positive expression and expanded. A suitable clone was selected based on genotypic and phenotypic characterization. |
| PnP-HEL23 | Y | Clone 1E9.03 was transfected with pX458 with gRNA-J and HEL23-2A HDR donor linearized. Cells were sorted for Cas9 positive expression (2A-BFP) and expanded. Cells were then sorted for surface IgH expression and expanded, and finally characterized for IgH and IgK expression. |

TABLE 1-continued

Summary of hybridoma clones

| Cell Type | Type | Description |
|---|---|---|
| PnP-HEL23-IgH⁻ | IgH⁻ | Clone Y was transfected with pX458 with gRNA-Q. Cells were sorted for Cas9 positive expression (2A-GFP) and expanded. A single cell sort for cells lacking surface IgH expression was performed followed by genomic PCR and Sanger sequencing to genotypically characterize the individual clones. A suitable clone was selected based on genotypic characterization. |
| PnP-HyHEL10 | U | Clone 1E9.C3 was transfected with pX458 with gRNA-J and HyHEL10- 2A HDR donor linearized. Cells were sorted for Cas9 positive expression (2ABFP) and expanded. Cells were then sorted for surface IgH expression and expanded, and then they underwent a second IgH sort. They were finally characterized for IgH and IgK expression. |
| PnP-EBV-2G4 | AA | Clone 1E9.03 was transfected with pX458 with gRNA-J and 2G4-2A HDR donor linearized. Cells were sorted for Cas9 positive expression (2A-BFP) and expanded. Cells were then sorted for surface IgH expression and expanded, and then they underwent a third sort for IgH and IgK expression. They were finally characterized for IgH and IgK expression. |
| PnP-EBV-4G7 | AB | Clone 1E9.C3 was transfected with pX458 with gRNA-J and 4G7-2A HDR donor linearized. Cells were sorted for Cas9 positive expression (2A-BFP) and expanded. Cells were then sorted for surface IgH expression and expanded, and then they underwent a third sort for IgH and IgK expression. They were finally characterized for IgH and IgK expression. |
| PnP-HEL23-2.0 | AC | Clone 1E9.C3 was transfected with pX458 with gRNA-J and HEL23-2A HDR donor linearized. Cells were NOT sorted for Cas9 positive expression. They were sorted for surface IgH expression and expanded. They were finally characterized for IgH and IgK expression. [In order to achieve a higher purity, cells were eventually sorted a second time for IgH and IgK expression] |
| PnP-mRuby-PA-AID | (winner selection in progress) | PnP-mRuby-pA cells were transfected with px458-BFP with gRNA-O and sorted for Cas9 expression (2A-BFP). Cells were then induced by 1 µg/ml Doxycycline, single-cell sorted for GFP expression, and characterized by further induction cycles (GFP+, mRuby knock-out activity), genotyping and transcript analysis. |
| PnP-mRuby-pA-IgH⁻ | (winner selection in progress) | PnP-HEL23-IgH⁻ cells were transfected with px458-BFP with gRNA-O and sorted for Cas9 expression (2A-BFP). Cells were then induced by 1 µg/ml Doxycycline, single-cell sorted for GFP expression, and characterized by further induction cycles, genotyping and transcript analysis. |

TABLE 2

List of gRNAs

| | Target region | Targeting sequence (5'-3' Sequence + PAM) | Resident plasmid |
|---|---|---|---|
| gRNA-A | Wen1.3 leader-VH intron | SEQ ID NO 01: GCTGTCGGGAGAAAGAAATTGTGG | pX458 |
| gRNA-B | Wen1.3 leader-VH intron | SEQ ID NO 02: GCCCTATCTCCTCTTCAGATTGG | pX458 |
| gRNA-C | Wen1.3 leader-VH intron | SEQ ID NO 03 GTTCCAATCTGAAGAGGAGATAGG | pX458 |
| gRNA-D | Wen1.3 JH downstream intron | SEQ ID NO 04 GGAGCATGACGGACTAATCTTGG | pX458 |
| gRNA-E | Wen1.3 JH downstream intron | SEQ ID NO 05 GTTGGTTTTAGCGGAGTCCCTGG | pX458 |
| gRNA-F | Wen1.3 VK leader | SEQ ID NO 06 GGAGAAGCAGGACCCATAGCAGG | pX458 |

TABLE 2-continued

List of gRNAs

| | Target region | Targeting sequence (5'-3' Sequence + PAM) | Resident plasmid |
|---|---|---|---|
| gRNA-G | Wen1.3 VK leader | SEQ ID NO 07<br>GGCTATGGGTCCTGCTTCTCTGG | pX458 |
| gRNA-H | Wen1.3 JH downstream intron | SEQ ID NO 08<br>GGGATCTTCTATTGATGCACAGG | pX458 |
| gRNA-I | Wen1.3 JH downstream intron | SEQ ID NO 09<br>GTGGCTAAATGAGCCATTCCTGG | pX458 |
| gRNA-J | mRuby2 | SEQ ID NO 10<br>GTCATGGAAGGTTCGGTCAACGG | pX458.2 (BFP) |
| gRNA-K | mRuby2 | SEQ ID NO 11<br>GCATGCCGTTGATCACCGCCTGG | pX458.2 (BFP) |
| gRNA-L | ROSA26 | SEQ ID NO 12<br>GAGACCTCCATCGCGCACTCCGGG | pX458 |
| gRNA-M | ROSA26 | SEQ ID NO 13<br>GCAGACCTCCATCGCGCACTCCGG | pX458 |
| gRNA-N | ROSA26 | SEQ ID NO 14<br>GCCTCGATGGAAAATACTCCGAGG | pX458 |
| gRNA-O | ROSA26 | SEQ ID NO 15<br>GCGATGGAAAATACTCCGAGGCGG | pX458 (BFP) |
| gRNA-P | ROSA26 | SEQ ID NO 16<br>AAGCATGTATTGCTTTACGTGGG | pX458 (BFP) |
| gRNA-Q | HEL23-2A CDR3 | SEQ ID NO 17<br>TGCGCGCGTGATAGCAGCGGCGG | pX458 |
| gRNA-R | HEL23-2A-IgH CDR3 | SEQ ID NO 18<br>ATTGCGCGCGTGATAGCAGGCGG | pX458 |

The sequences listed in this table (SEQ ID NO 01-SEQ ID NO 18) refer to the DNA sequences encoding the targeting sequences of the respective gRNAs.

METHODS

Hybridoma Cell Culture Conditions

The WT hybridoma cell line (Wen1.3) was obtained as a gift from Prof. Annette Oxenius (ETH Zurich). All hybridoma cell lines were cultivated in high-glucose Dulbecco's Modified Eagle Medium [(DMEM), Thermo Fisher Scientific (Thermo), 11960-044] supplemented with 10% heat inactivated fetal bovine serum [(FBS), Thermo, 10082-147)], 100 U/ml Penicillin/Streptomycin (Thermo, 15140-122), 2 mM Glutamine (Sigma-Aldrich, G7513), 10 mM HEPES buffer (Thermo, 15630-056) and 50 µM 2-mercaptoethanol (Sigma-Aldrich, M3148). All hybridoma cells were maintained in incubators at a temperature of 37° C. and 5% $CO_2$. Hybridomas were typically maintained in 10 ml of culture in T-25 flasks (Thermo, NC-156367), and split every 48/72 hours.

Cloning and Assembly of CRISPR-Cas9 Targeting Constructs

Unless otherwise noted, cloning of CRISPR-Cas9 plasmids and HDR donor constructs was done by Gibson assembly and cloning with the Gibson Assembly® Master Mix (NEB, E2611S) (Gibson et al., Nat Methods 2009, 6:343-345). When necessary, fragments for the Gibson assembly cloning were amplified with the KAPA HiFi HotStart Ready Mix [KAPA Biosystems (KAPA), KK2602].

All gRNAs were obtained from Integrated DNA Technologies (IDT) as single-stranded 5'-phosphorylated oligonucleotides purified by standard desalting. The basis for CRISPR-Cas9 experiments relied on the plasmid pSpCas9(BB)-2A-GFP (pX458), obtained as a gift from Feng Zhang (Addgene plasmid #48138) (Ran et al., Nat Protoc 2013, 8:2281-2308). An alternate version of pX458 was generated by replacing the GFP (eGFP variant) with BPF (TagBFP variant) (pX458.2 or pSpCas9(BB)-2A-BFP). For cloning gRNAs, both versions of pX458 were digested with Bbsl [New England BioLabs (NEB), R0539S], gRNA oligonucleotides were ligated into plasmids with DNA T4 ligase (NEB, M0202S). The gene or mRuby (mRuby2 variant) was derived from the plasmid pcDNA3-mRuby2, a gift from Michael Lin (Addgene plasmid #40260) (Lam et al., Nat Methods 2012, 9:1005-1012; Jinek et al., eLife 2013, 2:e00471-e00471). The HDR donors (mRuby and the antibody constructs) were cloned in the pUC57(Kan)-HDR plasmid, obtained from Genewiz. The vector was designed with homology arms according to the annotated mouse genomic sequence (GRCm38). The 2A antibody constructs were obtained as synthetic gene fragments (gBlocks, IDT). The HDR donor vectors were linearized by PCR with the KAPA HiFi HotStart ReadyMix (KAPA Biosystems, KK2602). All plasmid and linear versions of HDR donors, as well as pX458 and pX458-BFP, were ethanol precipitated as a final purification step.

Hybridoma Transfection With CRISPR-Cas9 Constructs

Hybridoma cells were transfected with the 4D-Nucleofector™ System (Lonza) using the SF Cell Line 4D-Nucleofector® X Kit L (Lonza, V4XC-2024) with the program CQ-104. Cells were prepared as follows: $10^6$ cells were isolated and centrifuged at 90×G for 5 minutes, washed with 1 ml of Opti-MEM® I Reduced Serum Medium (Thermo, 31985-062), and centrifuged again with the same parameters. The cells were finally re-suspended in 100 µl of total volume of nucleofection mix, containing the vector(s) diluted in SF buffer (per kit manufacturer guidelines). For the exchange of $V_H$ locus, 5 µg of pX458 (or pX458-BFP) with gRNA-E (targeting $V_H$) or gRNA-J (targeting mRuby), and 5 µg of the circular or linearized HDR donor constructs were nucleofected into cells. For $V_L$ deletion, 5 µg each of pX458 with gRNA-F and gRNA-H were co-transfected into cells. Following transfection, the cells were typically cultured in 1 ml of growth media in 24-well plates (Thermo, NC-142475). When a significant cell expansion was observed, cells were supplemented 24 hours later with 0.5-1.0 ml of fresh growth media. After sorting, typically 48 hours after transfection, cells were recovered in 24-well plates, and progressively moved into 6-well plates (Thermo, NC-140675) and T-25 flasks, following expansion. After replacing the $V_H$ with mRuby, cells were single-cell sorted in U-bottom 96-well plates (Sigma-Aldrich, M0812) in a recovery volume of 100 µl. The clones were eventually expanded in 24-well plates, 6-well plates and T-25 flasks.

Genomic and Transcript Analysis of CRISPR-Cas9 Targeting

Genomic DNA of hybridoma cell lines were recovered from typically 106 cells, which were washed with PBS by centrifugation (250×G, 5 minutes) and re-suspended in QuickExtract™ DNA Extraction Solution (Epicentre, QE09050). Cells were then incubated at 68 C for 15 minutes and 95 C for 8 minutes. For transcript analysis, total RNA was isolated from 106—5×106 cells. The cells were lysed with TRIzol® reagent (Thermo, 15596-026) and total RNA was extracted with the Direct-zol™ RNA MiniPrep kit (Zymo Research, R2052). Maxima Reverse Transcriptase (Thermo, EP0742) was used for cDNA synthesis from total RNA (Taq DNA Polymerase with ThermoPol® Buffer, NEB, M0267S). Both genomic DNA and cDNA were used as templates for downstream PCR reactions.

The gRNAs targeting WT IgH and IgK loci and mRuby were initially tested for their activity by 30 induction of NHEJ. The targeted fragment was amplified by PCR with KAPA2G Fast ReadyMix (KAPA, KK5121) and the PCR product digested with the Surveyor nuclease for the detection of mismatches (Surveyor® Mutation Detection Kit, IDT, 706020). For HDR evaluation, PCR was performed on genomic and cDNA using primers binding inside and outside homology arms, followed by fragment size analysis on DNA agarose gels. Selected PCR products were subjected to Sanger sequencing.

Flow Cytometry Analysis and Sorting of Hybridomas

Flow cytometry-based analysis and cell isolation were performed using the BD LSR Fortessa™ and BD FACS Aria™ III (BD Biosciences), respectively. At 24 hours post-transfection, approximately 100 µl of cells were harvested, centrifuged at 250×G for 5 minutes, resuspended in PBS and analyzed for expression of Cas9 (via 2A-GFP/-BFP). 48 hours post-transfection, all transfected cells were harvested and resuspended in Sorting Buffer (SB): PBS supplemented with 2 mM EDTA and 0.1% BSA). When labeling was required, cells were washed with PBS, incubated with the labeling antibody or antigen for 30 minutes on ice, protected from light, washed again with PBS and analyzed or sorted. The labeling reagents and working concentrations are described in table 3 below. For cell numbers different from $10^6$, the antibody/antigen and incubation volume were adjusted proportionally.

TABLE 3

Flow cytometry labeling reagents with their working concentrations

| Target antigen | Working conc. | Dilution from stock | Incubatn. volume | Fluorophore | Product ID |
| --- | --- | --- | --- | --- | --- |
| IgG2C | 3.3 µg/ml | 1:150 | 100 µl | Allophycocyanin (APC) | 115-135-208 (Jackson ImmunoResearch) |
| IgG2C | 1.6 mg/ml | 1:100 | 100 µl | AlexaFluor® 488 | 115-547-188 (Jackson ImmunoResearch) |
| IgK | 2.5 µg/ml | 1:80 | 100 µl | Brilliant Violet 421 ™ | 409511 (BioLegend) |
| Hen egg lysozyme | 0.1 µg/ml | 1:62.5 | 100 µl | AlexaFluor® 647 | 62971-10G-F (Sigma- Aldrich) |

Measurement of Antibody Secretion by ELISA

Sandwich ELISAs were used to measure the secretion of IgG from hybridoma cell lines. Plates were coated with capture polyclonal antibodies specific for $V_k$ light chains (goat anti-mouse, Jackson ImmunoResearch, 115-005-174) concentrated at 4 µg/ml in PBS (Thermo, 10010-015). Plates were then blocked with PBS supplemented with 2% w/v milk (AppliChem, A0830) and 0.05% v/v Tween®-20 (AppliChem, A1389) (PBSMT). Supernatants from cell culture ($10^6$ cells/sample, volume normalized to least concentrated samples) were then serially diluted (at 1:3 ratio) in PBS supplemented with 2% w/v milk (PBSM). As a positive control, a purified mouse IgG2b, K isotype control (BioLegend, 401202) was used at a starting concentration of 5 ng/µl (diluted in hybridoma growth media) and serially diluted as the supernatants. After blocking, supernatants and positive controls were incubated for 1 hour at RT or O/N at 4° C., followed by 3 washing steps with PBS supplemented with Tween-20 0.05% v/v (PBST). A secondary HRP-conjugated antibody specific for mouse Fc region was used (goat anti-mouse, Sigma-Aldrich, A2554), concentrated at 1.7 µg/ml in PBSM, followed by 3 wash steps with PBST. ELISA detection was performed using a 1-Step™ Ultra TMB-ELISA Substrate Solution (Thermo, 34028) as the HRP substrate. Absorbance at 450 nm was read with Infinite® 200 PRO NanoQuant (Tecan). For antigen specificity measurements, plates were coated with purified hen egg lysozyme (Sigma-Aldrich, 62971-10G-F) concentrated at 4

µg/ml in PBS. Blocking, washing, and supernatant incubation steps were made analogously to the previously described procedure, with the exception of serial dilutions of supernatants at 1:5 ratios. A secondary HRP-conjugated antibody was used specific for $V_k$ light chain (rat anti-mouse, Abcam, AB99617) concentrated at 0.7 µg/ml. ELISA detection by HRP substrate and absorbance reading was performed as previously stated.

Targeting of the ROSA26 Locus

Figure 1:
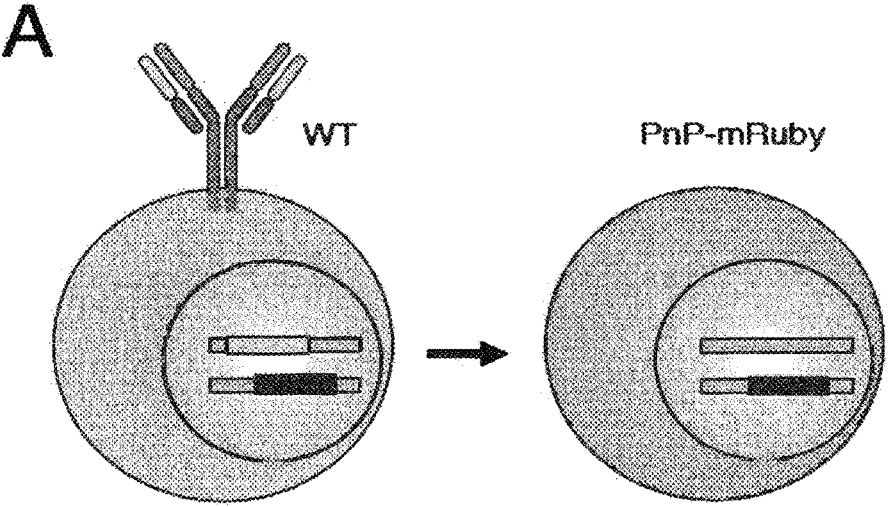
FIG. 1 shows the generation of PnP-mRuby cells. (A) Schematic shows wildtype (WT) hybridoma cells expressing antibody will be converted into PnP-mRuby. (B) Shown is the targeting of WT IgH genomic locus with the following annotations: leader sequence (L), mRNA splice sites (SS), $V_H$, and IgG constant heavy region (CH1). The CRISPR-Cas9 gRNA target site (black) is in the intron between $V_H$ and CH1. The donor construct consists of mRuby gene with a stop codon flanked by two homology arms of 732 and 711 bp. The PnP-mRuby IgH locus is generated by transfection of WT cells with CRISPR-Cas9 plasmid (pX458) and donor construct, which will result in HDR-based exchange of the $V_H$ region with mRuby. (C) Flow cytometry dot plot shows WT cells are exclusively IgH-positive and mRuby-negative, where PnP-mRuby cells are exclusively mRuby-positive and IgH-negative. (D) PCR was performed on genomic DNA from WT and PnP-mRuby cells using a forward primer in 5' HA and reverse primer that is external of the 3' HA. Agarose gel shows the expected size of bands. The band from PnP-mRuby cells was extracted and Sanger sequencing confirmed mRuby exchange of the $V_H$ region. (E) Shown is the targeting of WT hybridoma IgK locus with the following annotations: $V_L$, and IgK constant light region (CK), other annotations same as in shown in (A). Two gRNA target sites are utilized in order to delete the $V_L$ region. (F) Flow cytometry dot plot shows WT cells are strongly IgH- and IgK-positive, where PnP-mRuby cells are exclusively IgH- and IgK-negative. (E) PCR was performed on genomic DNA from WT and PnP-mRuby cells using a forward primer 5' of the gRNA-F site and reverse primer 3' of gRNA-H site. Agarose gel shows the expected size of band for WT cells and nearly no amplification product for the PnP-mRuby cell line. Throughout this figure, WT cells correspond to clone WEN1.3 and PnP-mRuby cells correspond to clone 1E9.C3 (see table 1).
Figure 1:
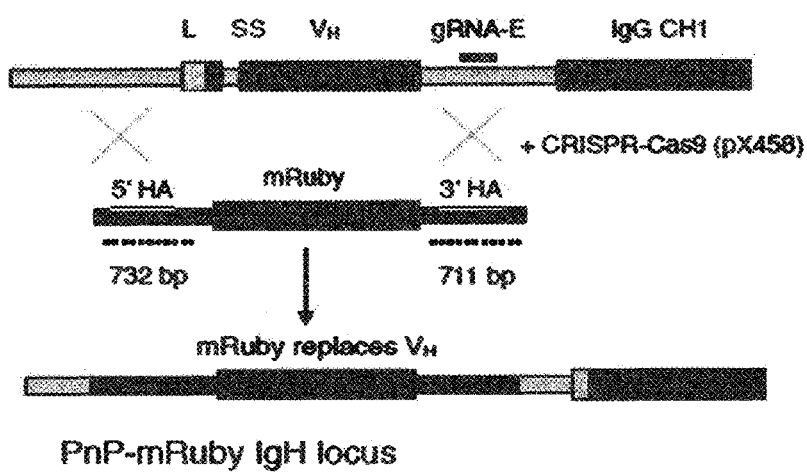
Figure 1:
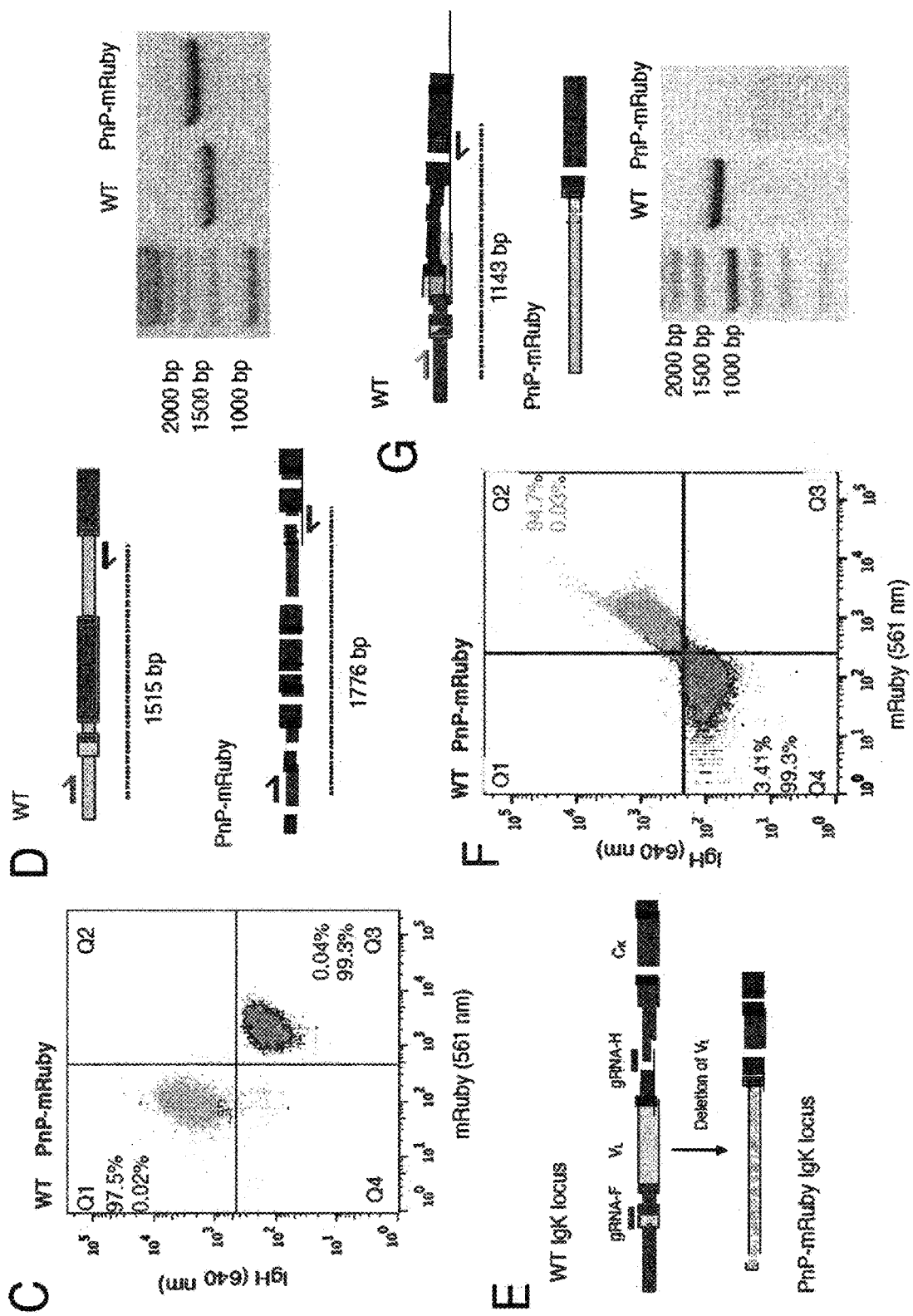
Figure 2:
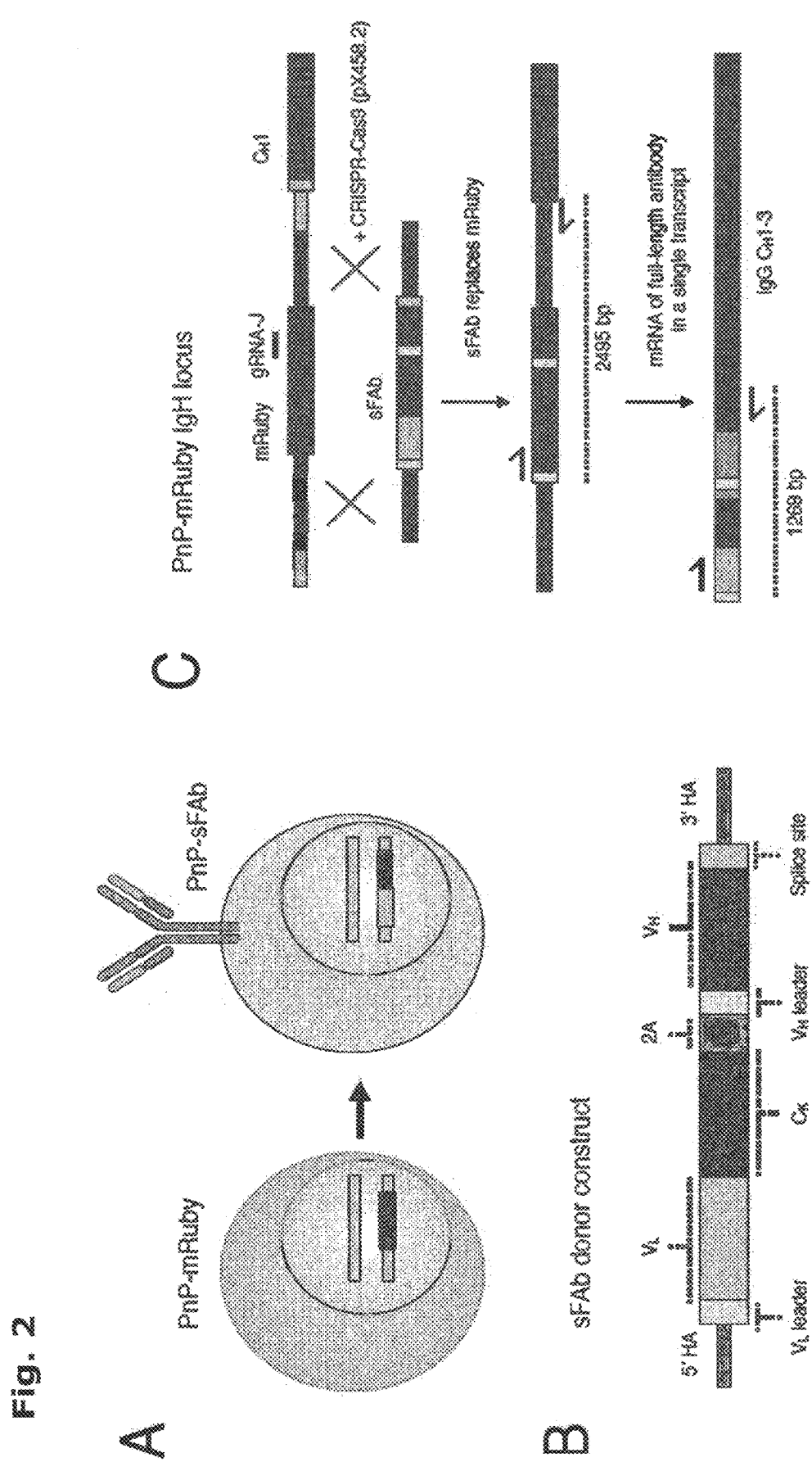
FIG. 2 shows the generation of PnP-mRuby hybridomas reprogrammed to surface express and secrete a new antibody. (A) Schematic shows PnP-mRuby cells expressing mRuby will be converted back into hybridomas expressing a new antibody via sFAb. (B) Shown is simplified design of the sFAb donor construct (for complete design details, see FIG. S8). (C) Shown is the PnP-mRuby IgH locus where gRNA-J target site is in the mRuby gene. PnP-mRuby cells transfected with pX458.2 and sFAb donor will result in HDR-driven genomic replacement of mRuby. The new antibody will then be expressed on a single mRNA transcript. (D) Flow cytometry dot plot shows the different populations that emerge following transfection of PnP-mRuby with pX458 and sFAb donor. Cells which were positive for IgH expression were sorted. (E) Flow cytometry dot plot shows initial population of PnP-mRuby cells and resulting cells (PnP-HEL23) from sorted IgH-positive population in (D), which are now strongly positive for IgH and IgK expression. (F) Graph shows sandwich ELISA results (capture anti-IgK, primary detection anti-IgH) on hybridoma culture supernatant, PnP-HEL23 show IgG secretion levels similar to WT. (G) PCR was performed on the genomic DNA of WT, PnP-mRuby, PnP-HEL23 cells using primers shown in (C). Agarose gel from genomic PCR shows the predicted band size in PnP-HEL23. (H) RT-PCR from mRNA results in a visible band present of the correct size present only in PnP-HEL23. The bands from PnP-HEL23 were extracted and Sanger sequencing confirmed correct integration of the PnP-sFAb construct. Throughout this figure, WT cells correspond to clone WEN1.3, PnP-mRuby cells correspond to clone 1E9.C3, and PnP-HEL23 correspond to clone Y (see table 1).
Figure 2:
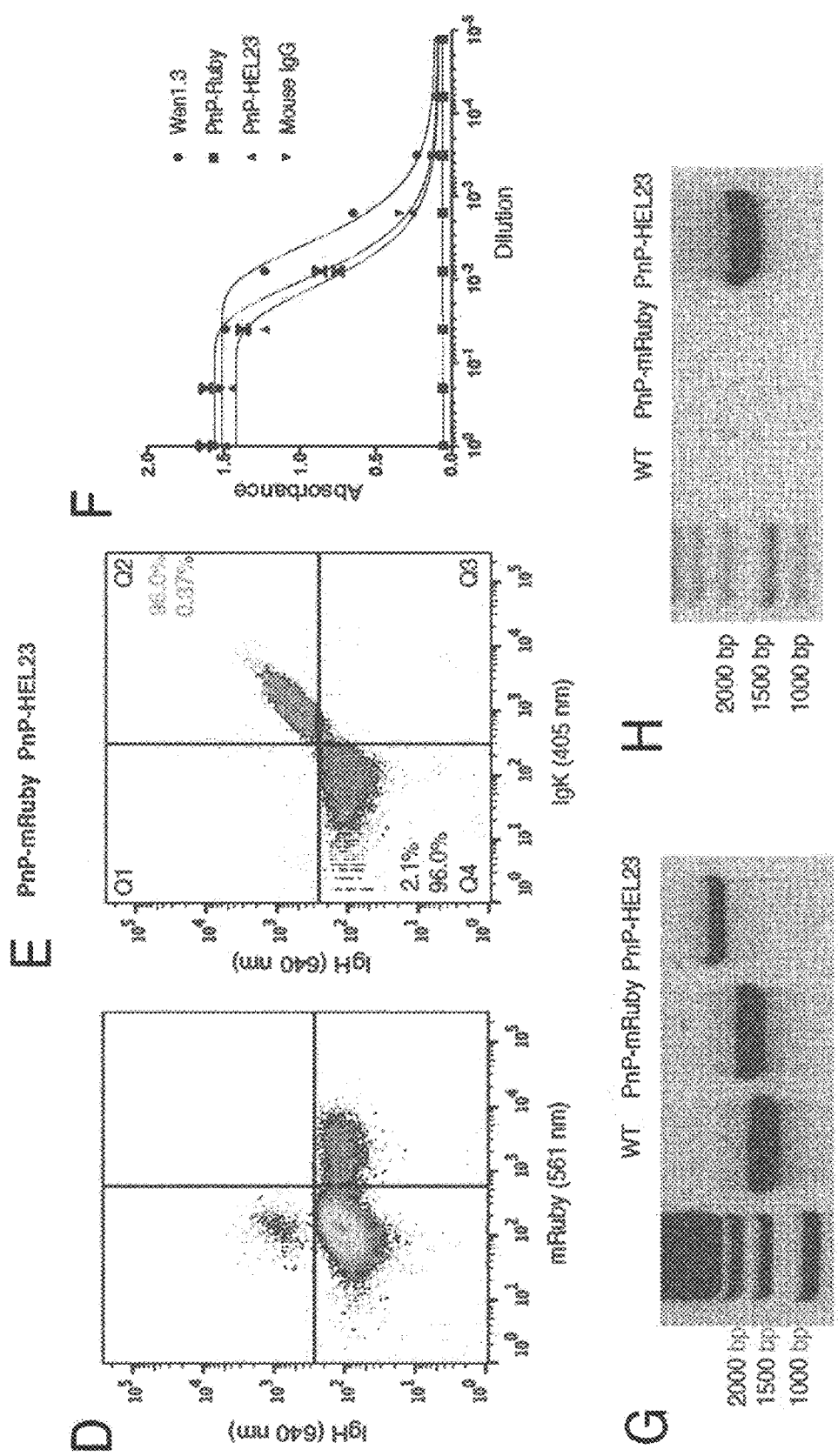
Figure 3:
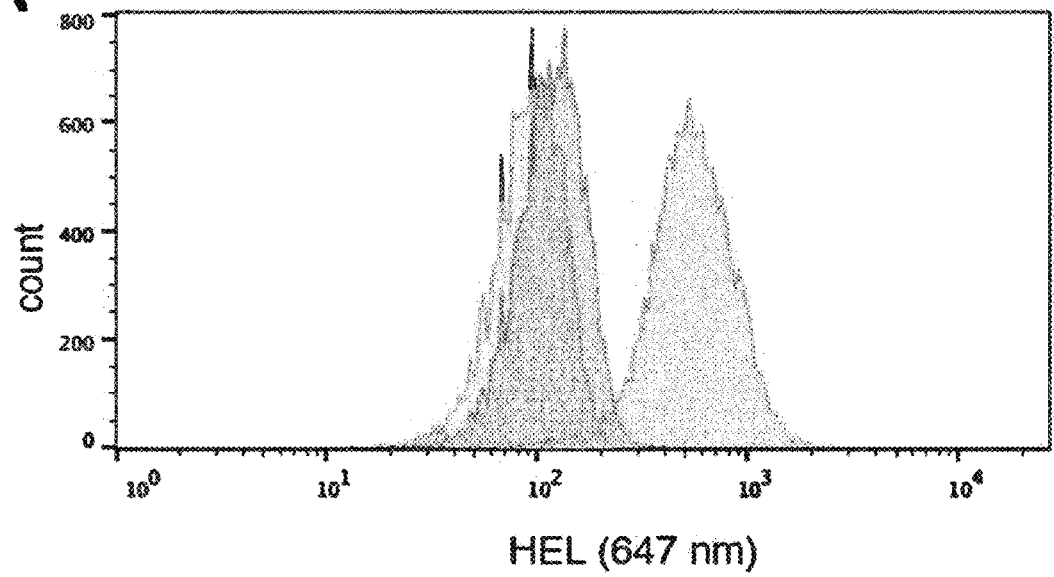
FIG. 3 shows PnP-HEL23 cells that surface express and secrete an antigen-specific antibody. (A) Flow cytometry histogram shows PnP-HEL23 cells surface express antibody specific for cognate antigen HEL. (B) ELISA data shows that PnP-HEL23 cells secrete antibody specific for HEL. WT cells correspond to clone WEN1.3, PnP-mRuby cells correspond to clone 1E9.C3, PnP-IgG cells correspond to clone Y (see table 1).
Figure 3:
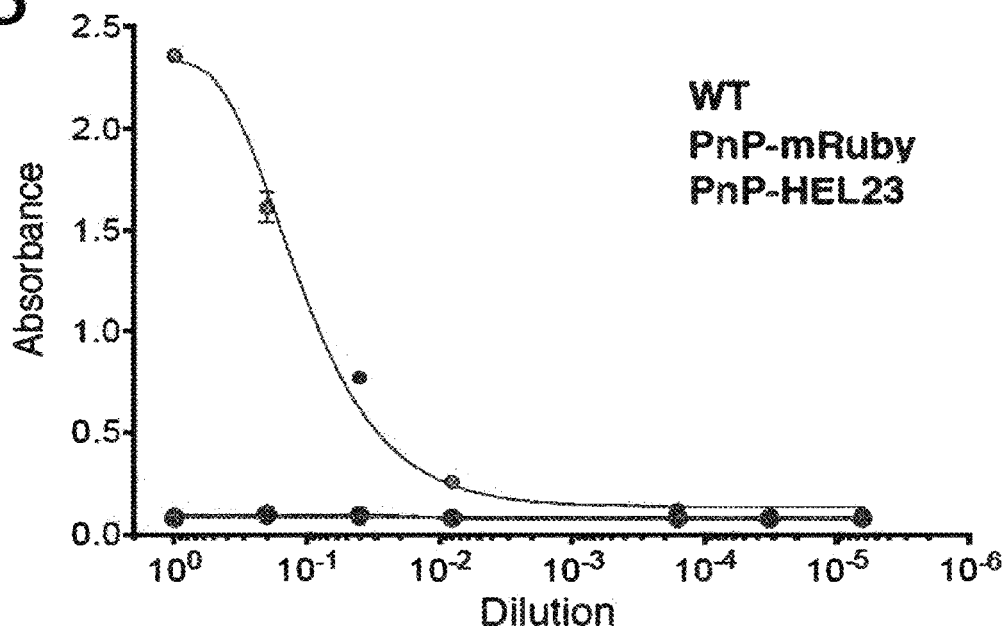
Figure 4:
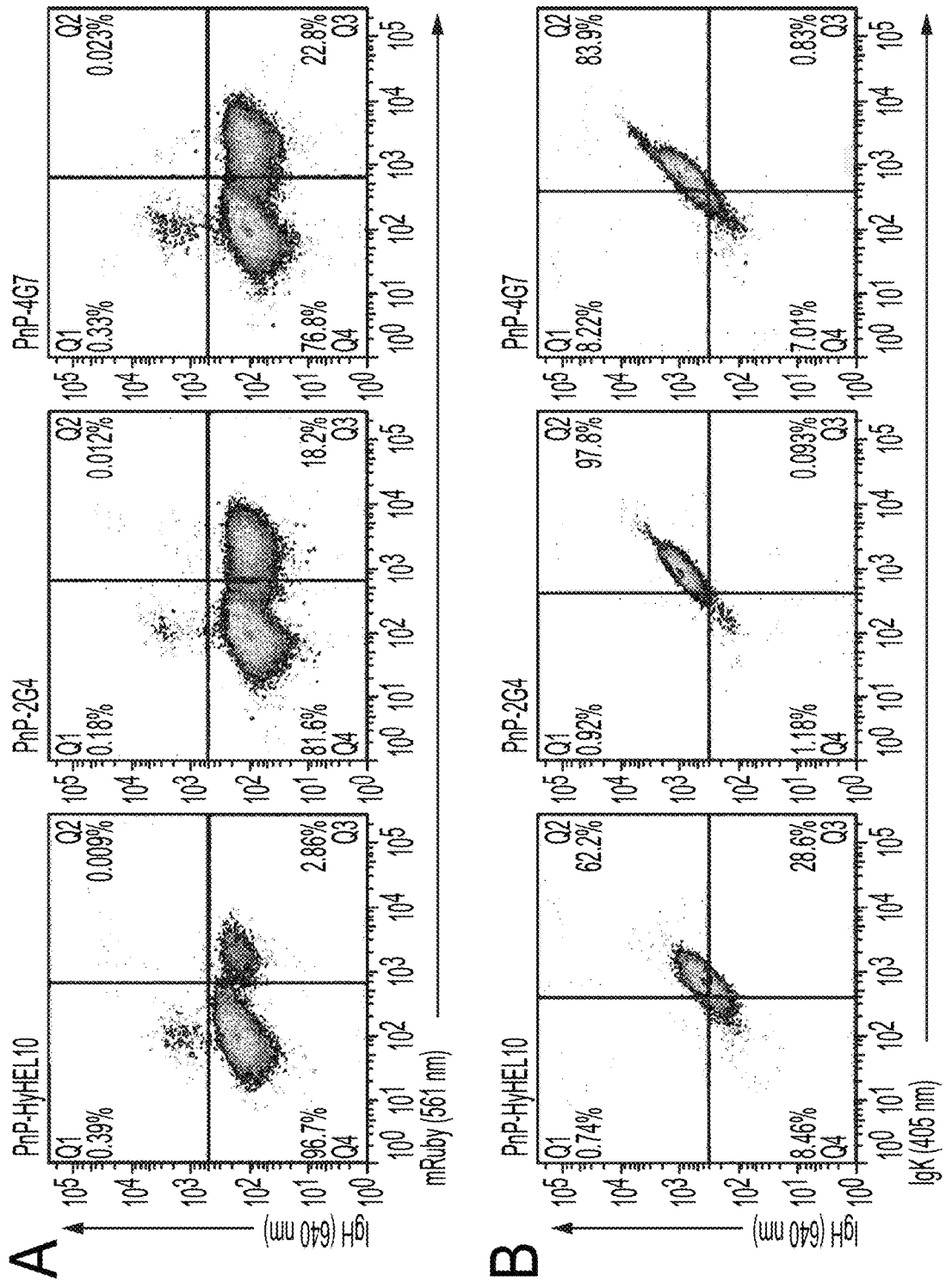
FIG. 4 shows the rapid and reproducible generation of PnP-antibody producing cells. (A) Flow cytometry dot plot shows PnP-mRuby following transfection with pX458.2 and different PnP-sFAb donor constructs. Cells were sorted for IgH expression. (B) Flow cytometry dot plots show that all three PnP cell lines express IgH and IgK following sorting in (A). (C) As in FIGS. 2G and 2H, PCR and RT-PCR was performed on genomic DNA and mRNA, respectively. (D, E) Similar to (A) and (B) are flow cytometry dot plots for PnP-HEL23.2 cells, with the exception that Cas9 sorting step was omitted. PnP-HyHEL10 corresponds to clone U, PnP-EBV-2G4 corresponds to clone AA, and PnP-EBV-4G7 corresponds to clone AB, PnP-HEL23 corresponds to clone AC (see table 1).
Figure 4:
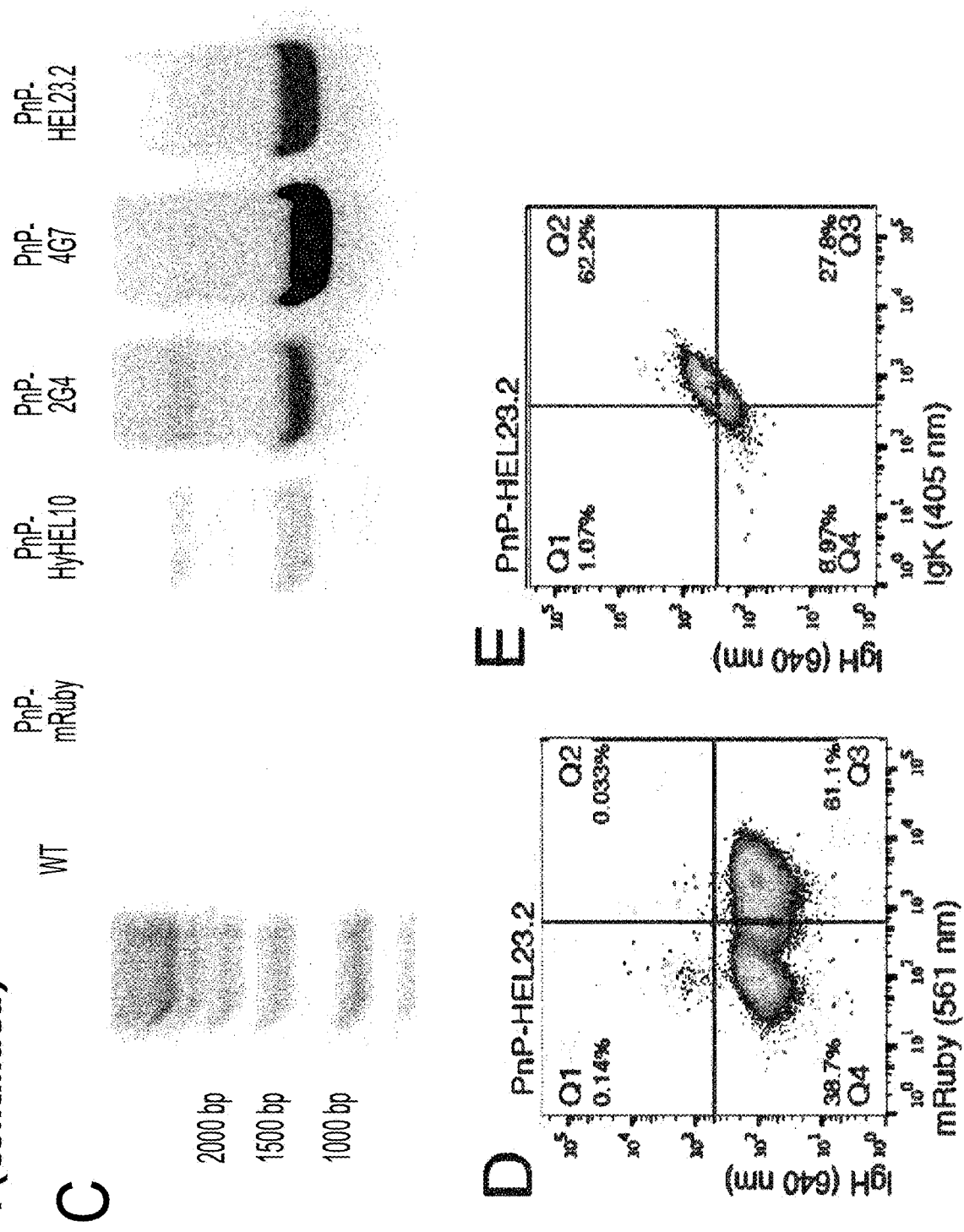
Figure 5:
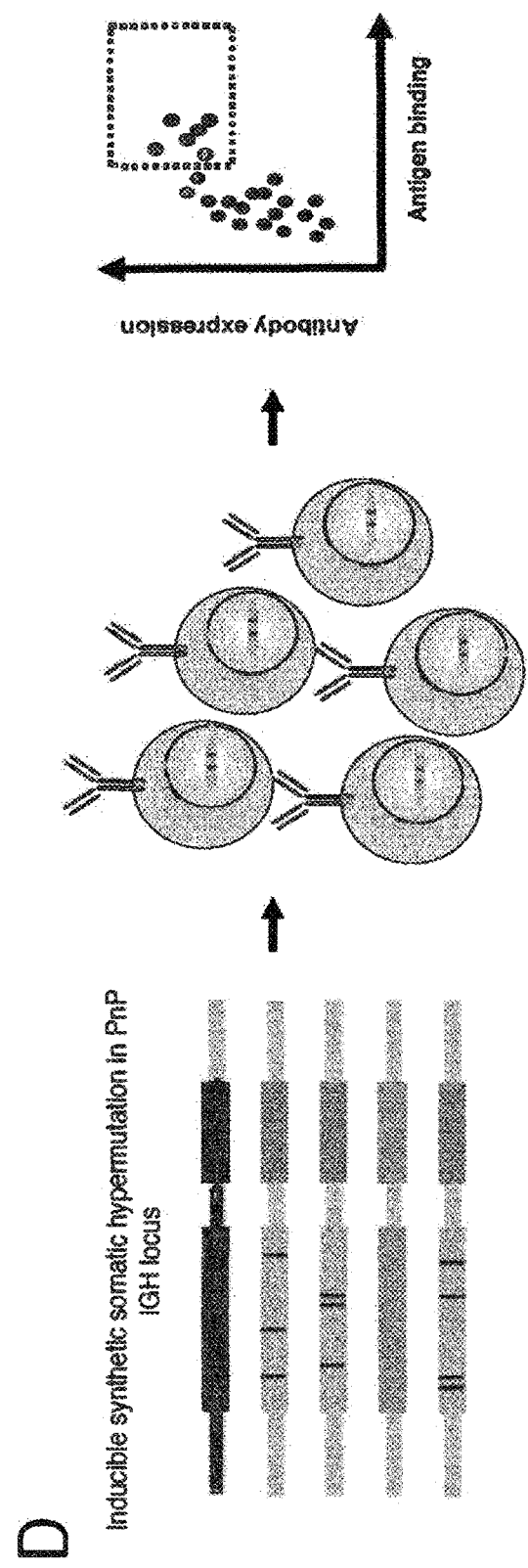
FIG. 5 shows the generation of PnP hybridoma cell that express Cas9 and AID. (a) Shown is the CRISPR-Cas9 targeting of PnP-mRuby Rosa 26 locus. A donor construct will provide Cas9 gene with the 2A peptide and puromycin resistance gene. Integration into this locus will provide constitutive expression of Cas9 in all PnP-mRuby cells. (b) and (c) Shown is the integration of an inducible AID locus into PnP-mRuby-Cas9 cells, either by integration into the Rosa26 locus or into the native AID locus. (d) Schematic shows that large libraries will be generated by inducible synthetic somatic hypermutation via expression of AID. These libraries can then be used for directed evolution and high-throughput screening by flow cytometry.
Figure 6:
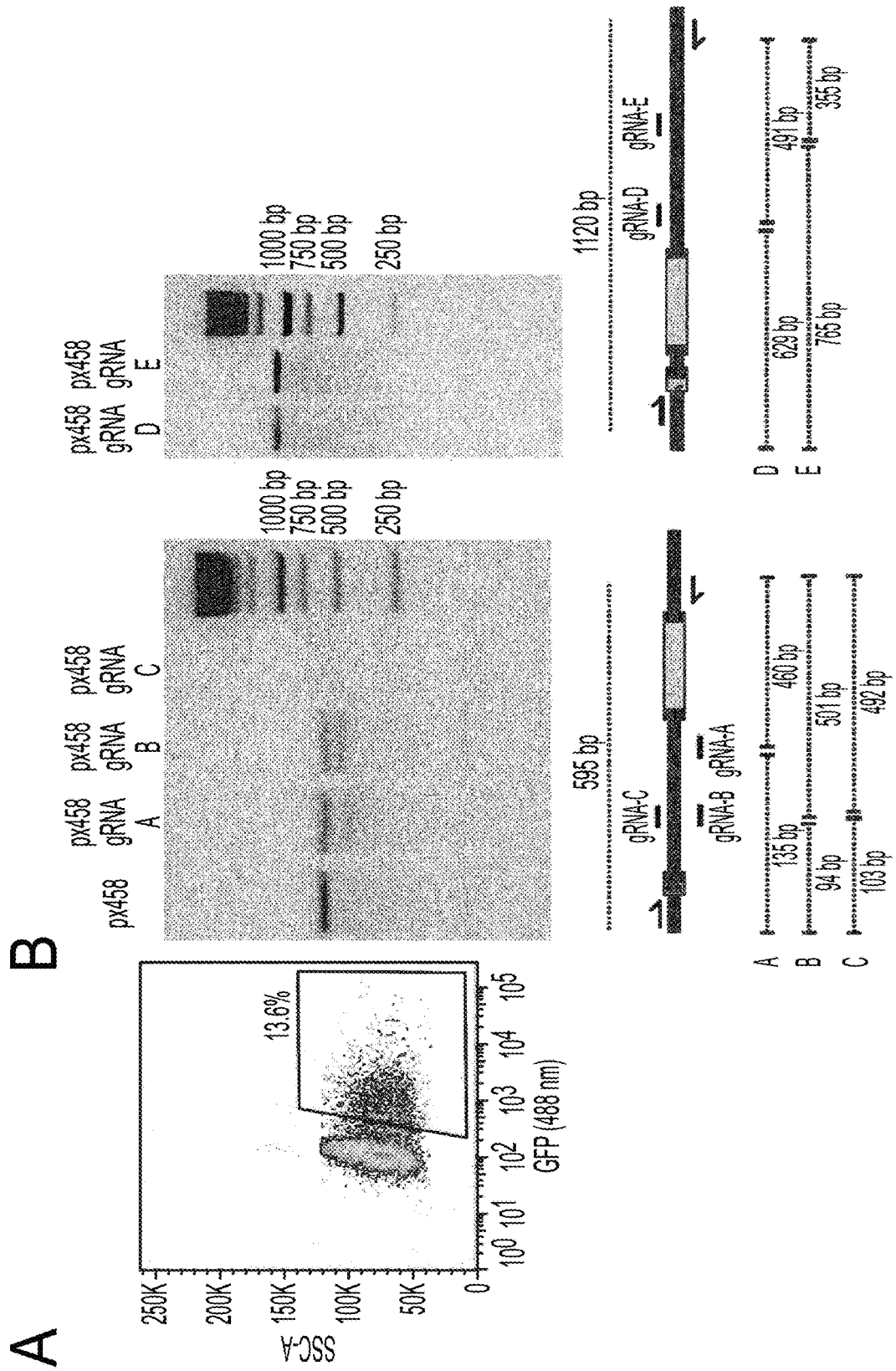
FIG. 6 shows the validation of CRISPR-Cas9 targeting of immunoglobulin loci of hybridoma cells. (A) Flow cytometry dotplot shows expression of Cas9-2A-GFP in WEN1.3 cells following transfection with with pX458. (B) Surveyor results validate CRISPR-Cas9 targeting in IgH locus (agarose gels of all gRNA sites tested). (C) Surveyor results validate CRISPR-Cas9 targeting in IgK locus (agarose gels of all gRNA sites tested).
Figure 6:
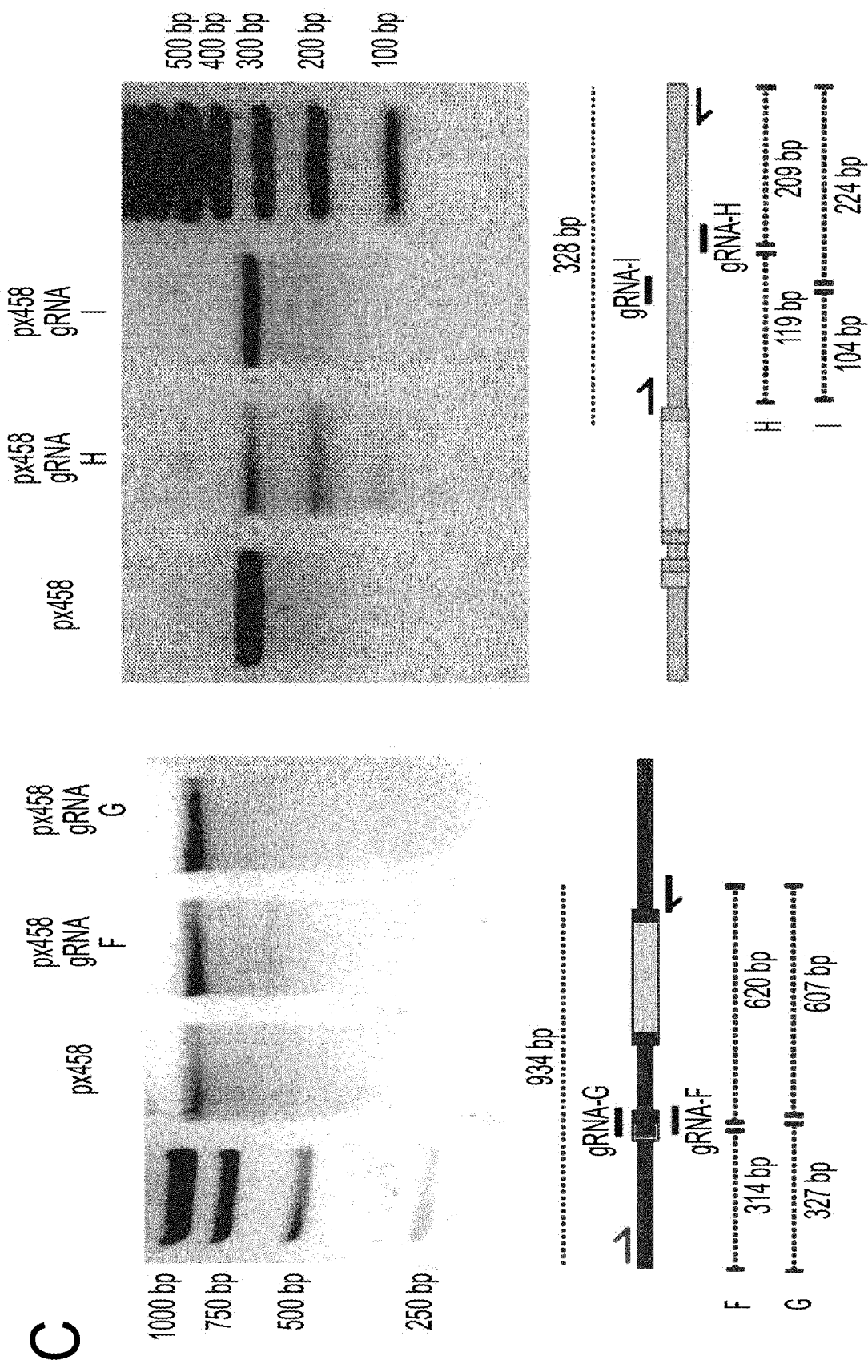
Figure 7:
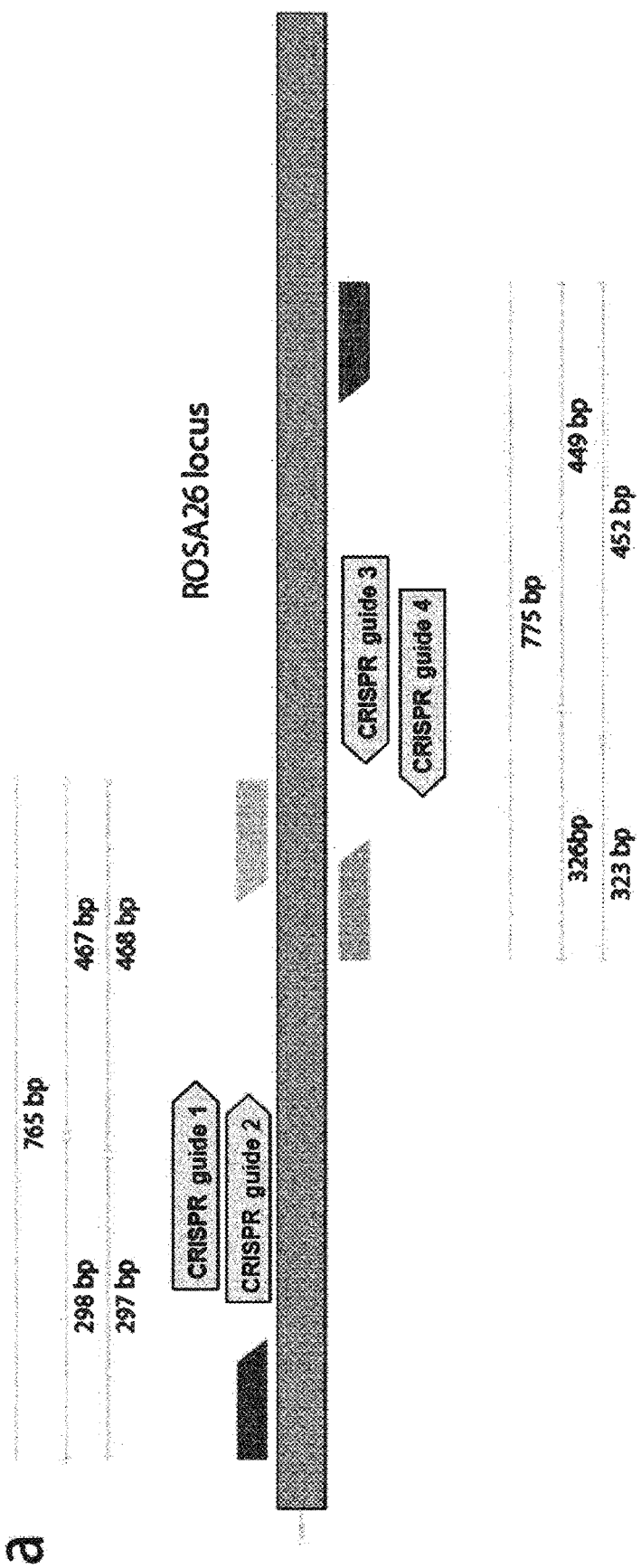
FIG. 7 shows targeting of the ROSA26 locus by CRISPR-Cas9. (A) ROSA26 locus (mouse chromosome 6) with CRISPR targets identified; displayed are also the primers used for fragment amplification for cleavage analysis. (B) DNA gels from Surveyor assay showing that all 4 tested guides induce successful CRISPR cleavage. The fragments match the expected size, shown in (A).
Figure 7:
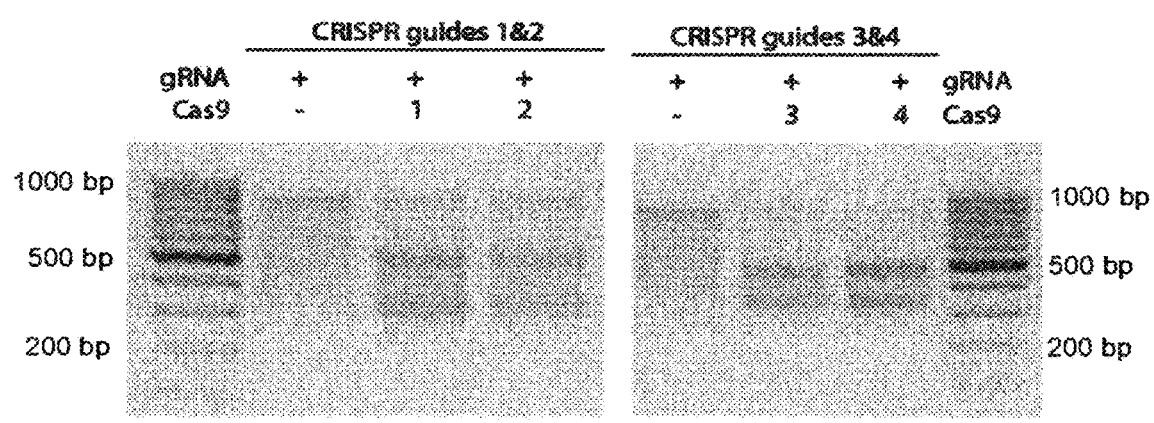

The mouse safe harbor locus ROSA26 was amplified and Sanger sequenced from Wen1.3 cells, and the sequence obtained was used to design DNA cassette homology arms. Guide RNA target sequences (gRNA-L to gRNA-P) were individually validated by Surveryor Assay (FIG. 7). This locus was targeted for the creation of the PnP-mRuby-AID, PnP-IgG-AID and the PnP-mRuby-Cas9 cell lines.

Figure 9:
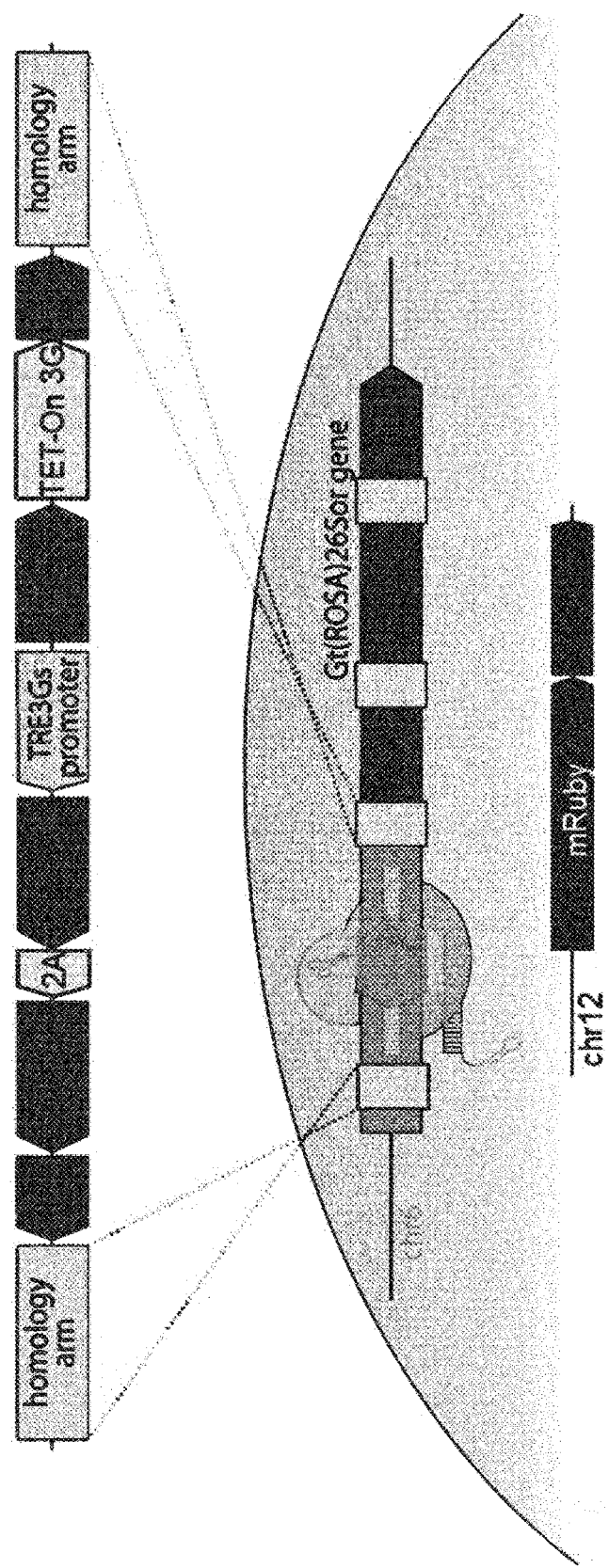
FIG. 9 shows generation and selection of PnP-iAID-mRuby cell lines. (A) Shown is the integration of the iSSHM donor cassette (GFP-2A-AID construct under a Doxinducible promoter system) is integrated into the Rosa26 locus of hybridoma cells by Cas9-induced HDR. Hybridoma cells express mRuby in their reprogrammed IgH locus. (B) Cell expressing Cas9 (2A-BFP) are sorted, then in the presence of Dox (or absence for negative controls), GFP-positive cells are single cell sorted and expanded. (C) Characterization of GFP expression with or without Dox in the single-cell sorted colonies from B.
Figure 9:
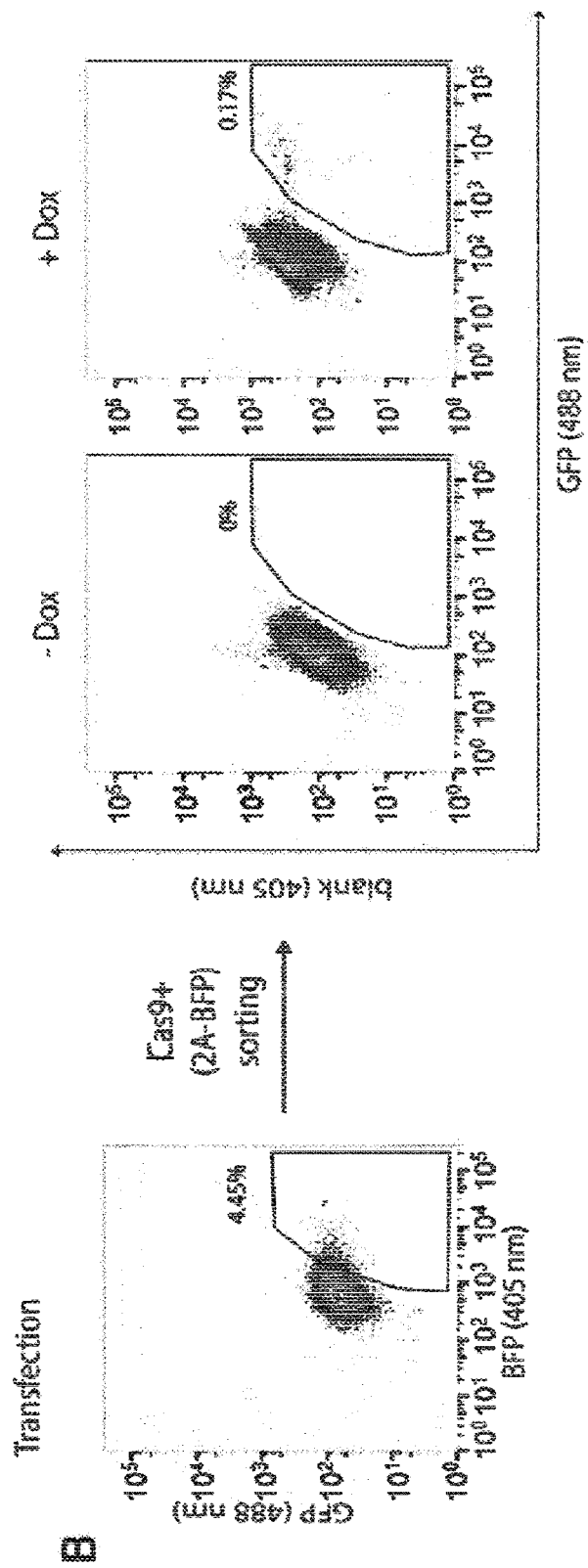
Figure 9:
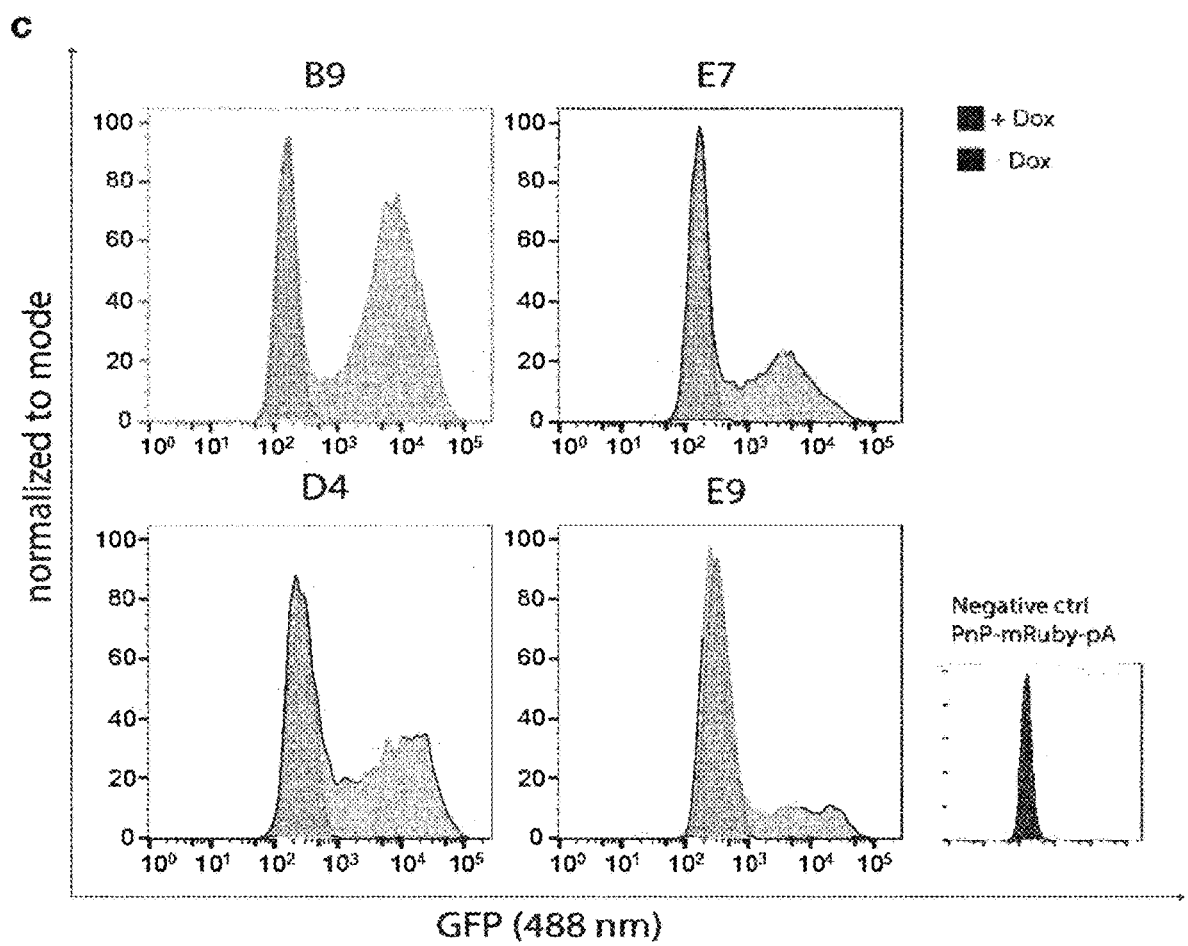
Figure 10:
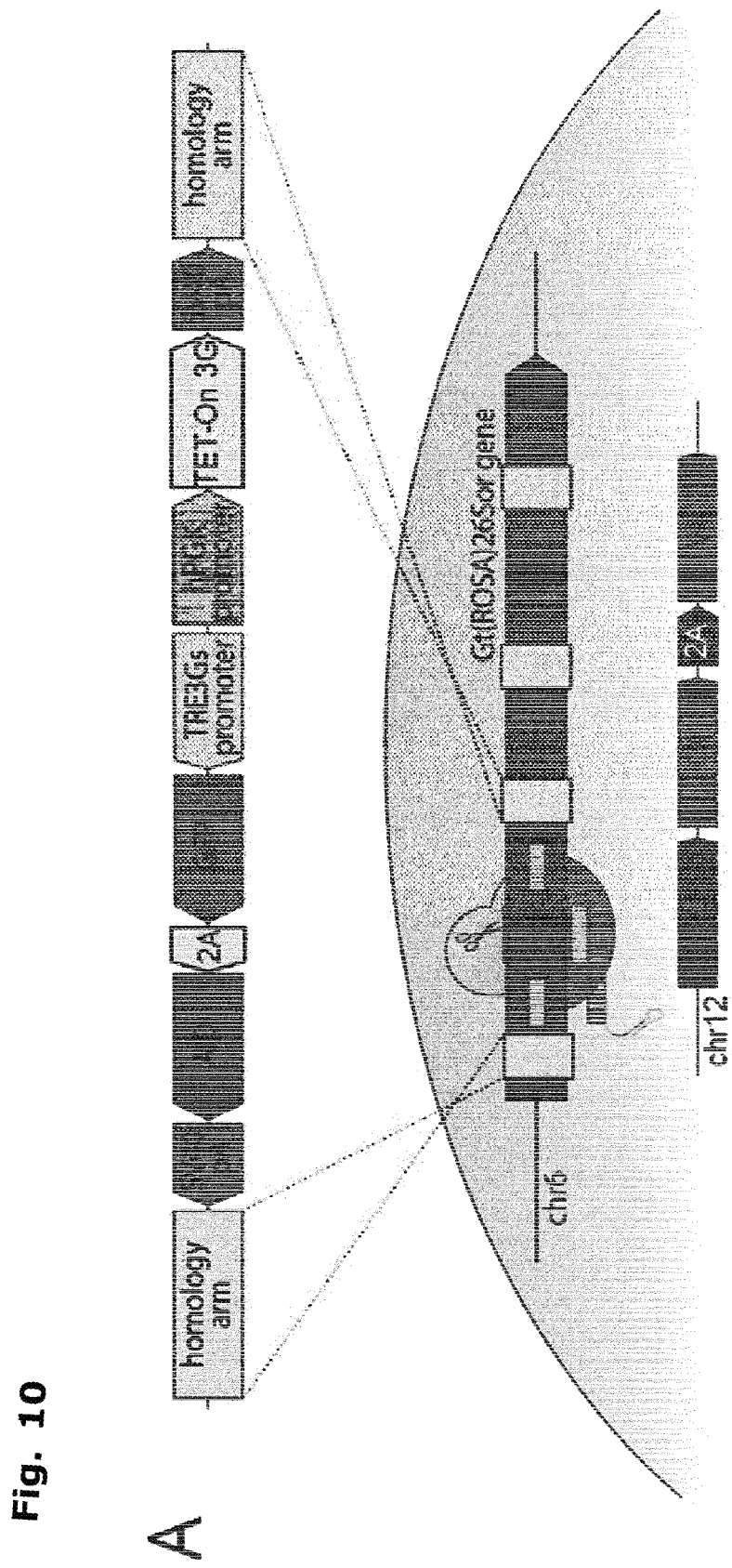
FIG. 10 shows generation and selection of PnP-iAID-IgG cell lines. (A) Shown is the integration of the iSSHM donor cassette (GFP-2A-AID construct under a Doxinducible promoter system) is integrated into the Rosa26 locus of hybridoma cells by Cas9-induced HDR. Hybridoma cells express IgG through sFAb in their reprogrammed IgH locus. (B) Cell expressing Cas9 (2A-BFP) are sorted, then in the presence of Dox (or absence for negative controls), GFP-positive cells are single cell sorted and expanded. (C) Characterization of GFP expression with or without Dox in the single-cell sorted colonies from B.
Figure 10:
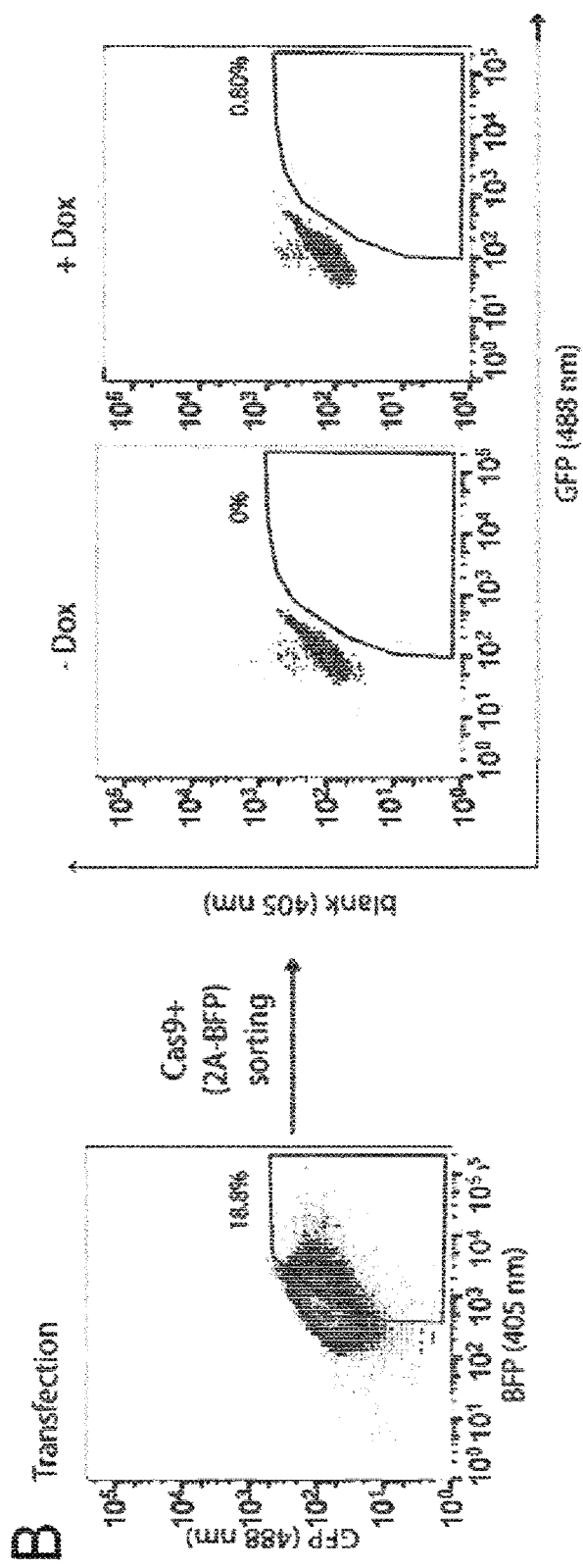
Figure 10:
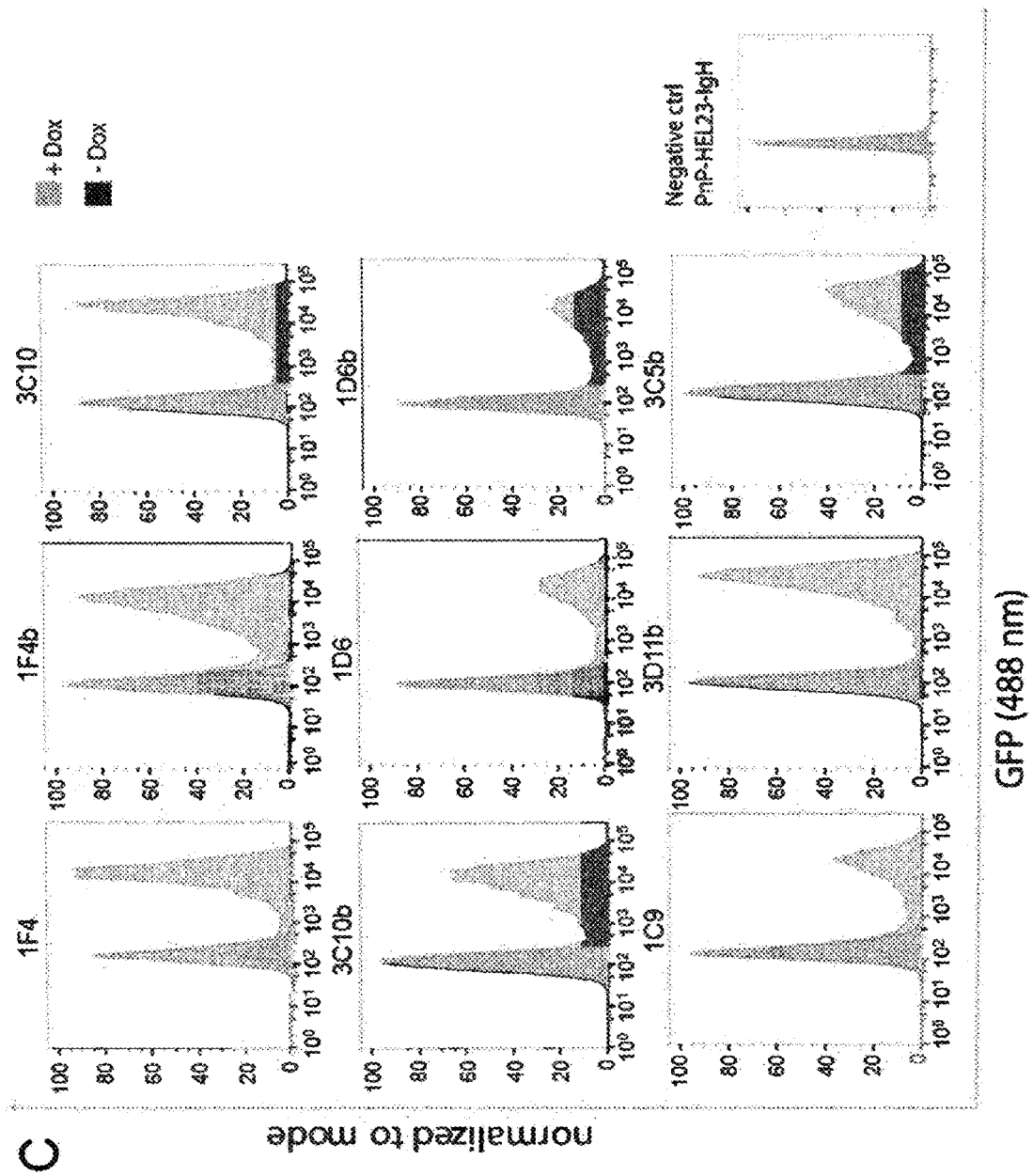
Figure 11:
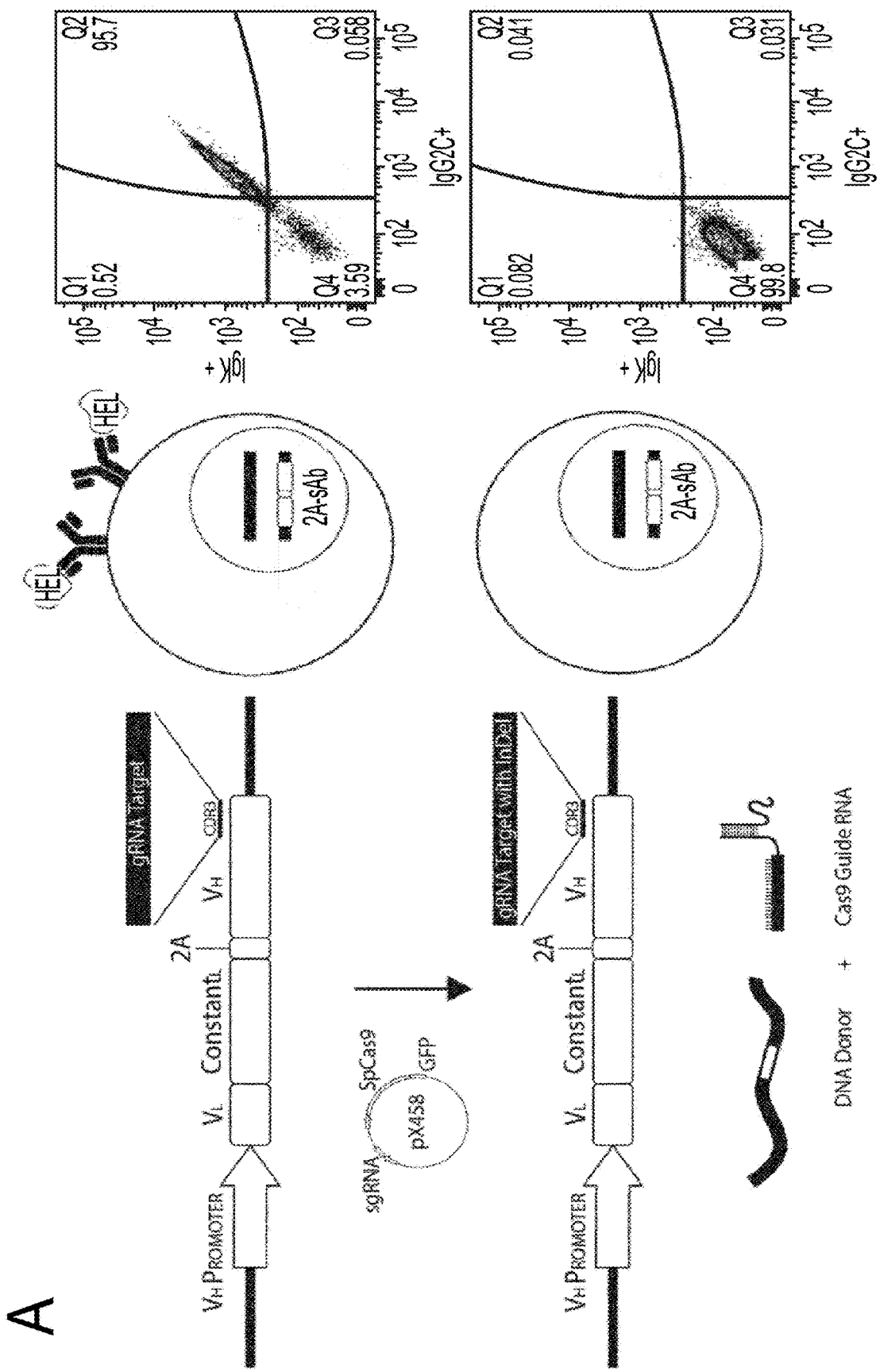
FIG. 11 shows the general workflow for optimizing ssODN induced HDR and constructing a synthetic antibody (sAb) library with CDRH3 genetic diversity. (A) A.I: PnP-HEL23 sAb construct in the heavy chain gene locus with a CDRH3 sgRNA site to direct cleavage by Cas9 following transfection with the Cas9 vector, pX458. The Cas9 induced double stranded break introduces insertions/deletions (In-Deis) near the cut site through NHEJ causing a frameshift mutation and dysfunctional protein expression. The sequence shown in exploded view is SEQ ID No 17. A.IIa: Antibody expression can then be restored through HDR promoted by donor ssODNs with codon rearrangements for the CDRH3. A.IIb: Additional genetic diversity into the CDRH3 of the sAb cassette through HDR incorporation of degenerate ssODNs (NNK randomization). Sorting results: upper left: A1 upper panel; upper right: A1 lower panel (≙ A.IIa/b upper panel); lower left: A.IIa lower panel; A.IIb lower panel.
Figure 11:
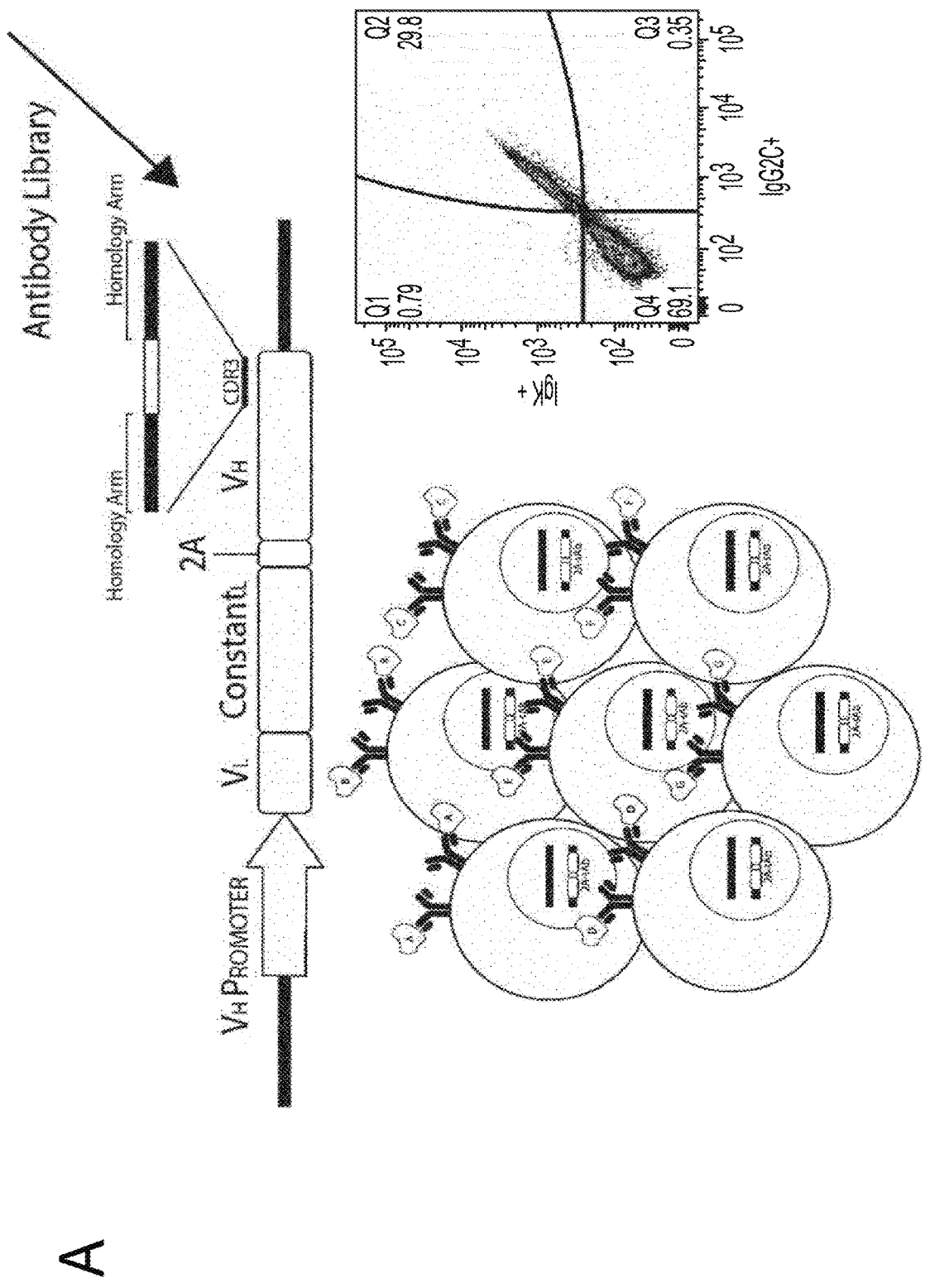
Figure 11:
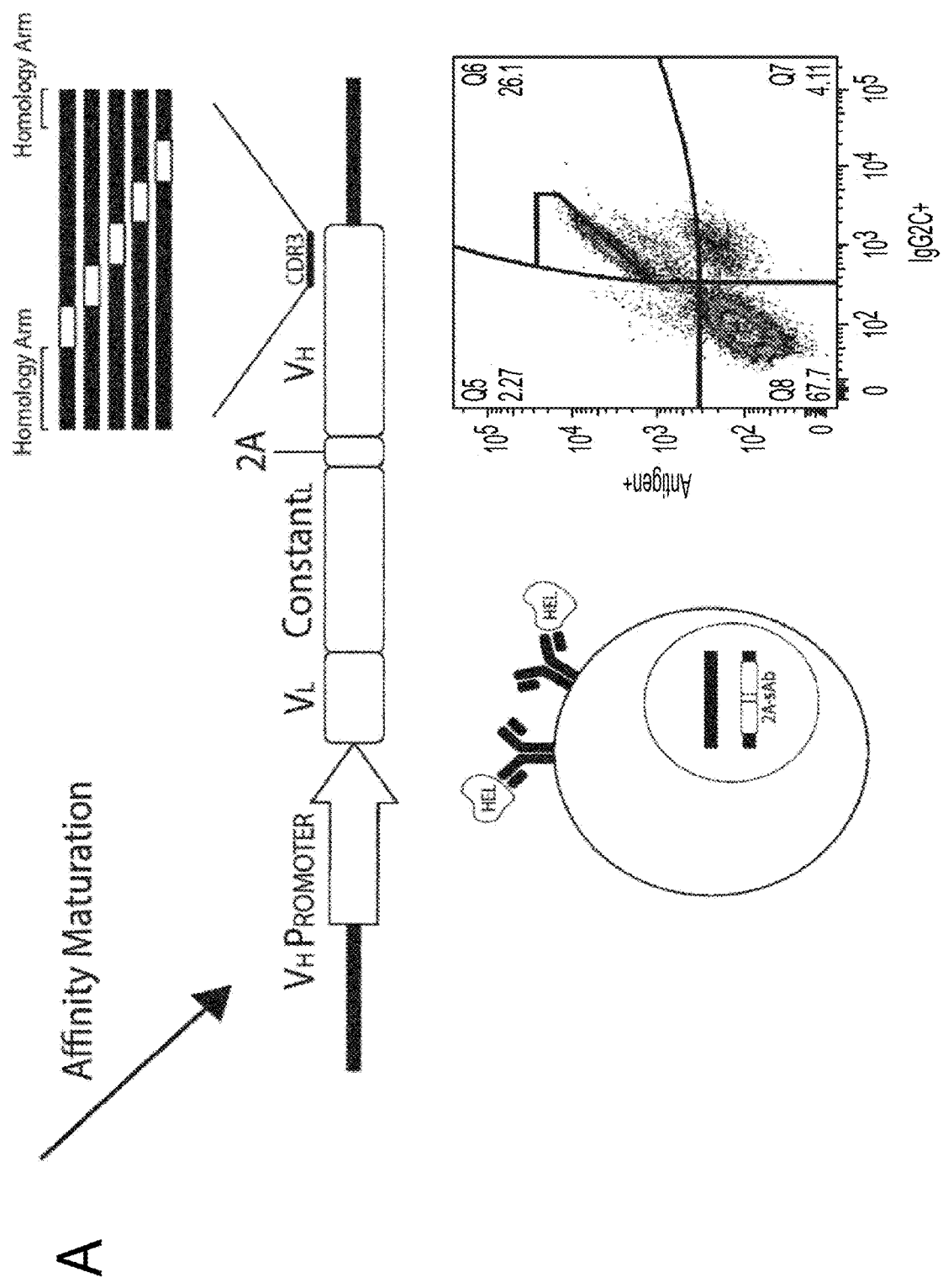
Figure 11:
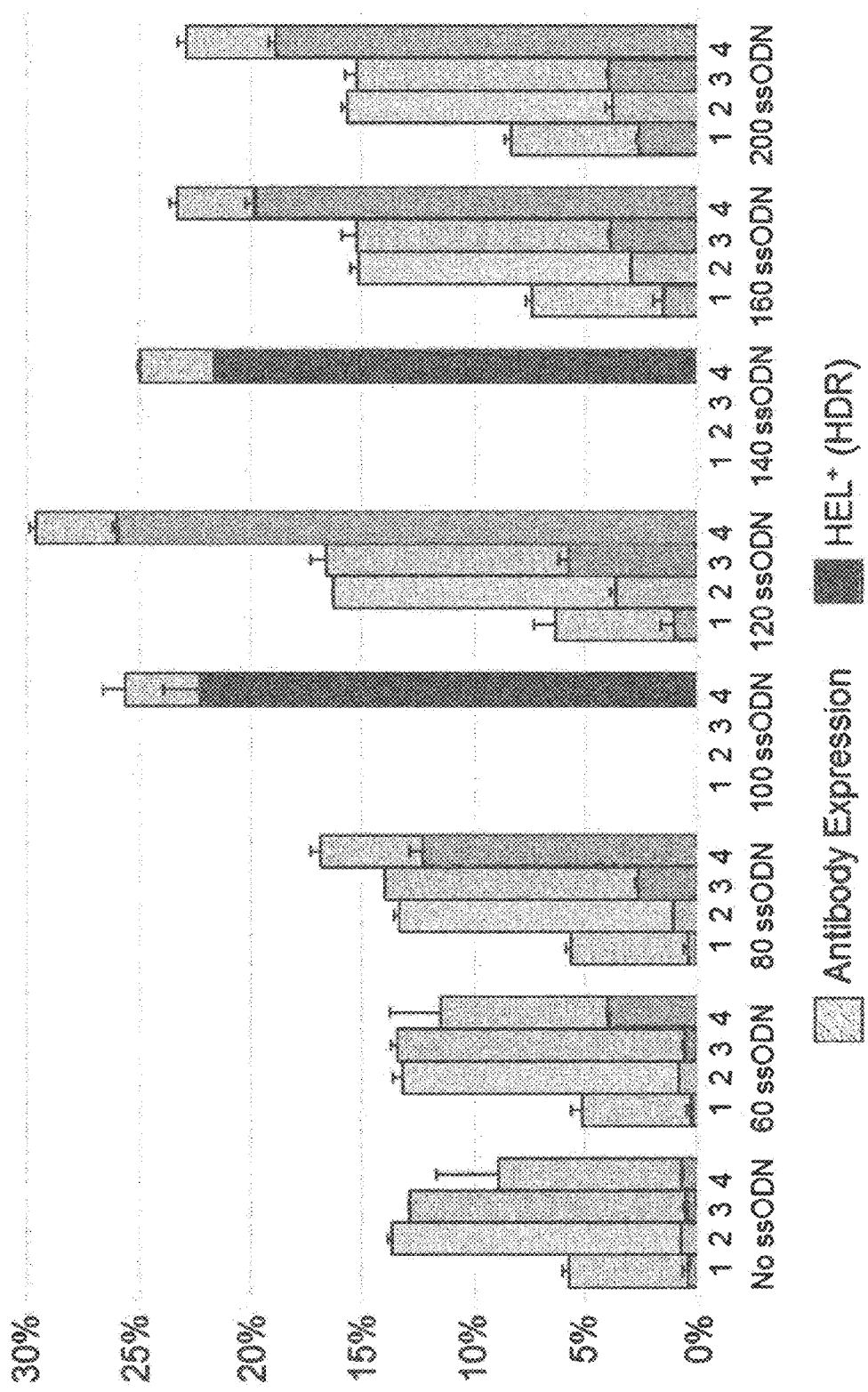

For the targeting of the ROSA26 in the creation of the PnP-mRuby-AID and the PnP-mRuby-Cas9 cell lines, gRNA-O and gRNA-P were selected due to their high cleavage efficiency. Generation of the AID cell lines and induction by Doxycycline Cloning of the donor cassette for the inducible AID (iSSHM) system was performed in three steps. (1) The Tet-One™ Inducible Expression System was purchased from Takara Clontech (634301); GFP-2A-AID was obtained as synthetic gene fragment (gBlocks, IDT) and cloned into the pTetOne vector by Gibson assembly cloning. (2) Homology arms (829 and 821 bp) for the hybridoma's ROSA26 locus were obtained by genomic DNA PCR and cloned in a pUC57(Kan) plasmid. (3) Finally, the previously cloned—see point (1)—Tet-One-GFP-2A-AID construct (containing, in the forward orientation: the human phosphoglycerate kinase 1 promoter (hPGK), the Tet-On 3G transactivator protein, and the SV40 poly-A signal; in the reverse orientation: the $P_{TRE3GS}$ Inducible promoter, the GFP-2A-AID construct and the SV40 poly-A signal) was inserted between the homology arms through Gibson assembly cloning. The HDR donor was linearized by PCR with restriction digestion with the enzyme AjuI (Thermo, ER1951). gRNA-O was obtained and cloned as previously described in pX458-BFP. As an alternative NHEJ insertion design, the TetOne-GFP-2A-AID construct is linearized without homology arms. The cell lines engineered for introduction of the TetOne-iSSHM system are: PnP-mRuby-pA (PnP-mRuby with a bGH poly-A tail); PnP-HEL23-IgH⁻ (PnP-HEL23 with a frameshift insertion in the HCDR3 knocking out antibody expression—see next sections). The workflow for these cells are shown in FIGS. 9 and 10.

a. Cell Lines Generation

From the transfection stage, the cells were kept in Tet-free GM: regular growth media supplemented with Tet System Approved FBS, US-sourced (Takara Clontech, 631105). PnP-HEL23-IgH⁻ and PnP-mRuby-pA cells were transfected with ~2.5 µg px458-BFP with gRNA-O and 2.5 µg linearized pTetOne-HDR donor (see previous section). 48 hours after transfection the cells were sorted for BFP and grown for recovery. Once recovered, induction experiments were performed to verify the system's functionality: Doxycycline (Takara Clontech, 631311) was dissolved in nuclease-free $H_2O$ at 1 mg/ml, sterile filtered and diluted in Tet-free GM at need directly before use. Concentrations in the range between 1 ng/ml and 2 µg/ml were tested, with 1 µg/ml proving to be the most efficient. Cells were induced by incubation at 37 C for 24 or 48 hours; however, 24 hour incubation gave the best results and was selected as main condition to check for positive integration and induction efficiency.

The cells were sorted after 24 hours of induction: from the GFP positive population, single-cell clones were isolated, grown and characterized. An initial screening was performed to select the most positive clones after Dox induction: each sample was seeded at 1 µg Dox/$10^5$ cells/1 ml culture and screened for GFP 24 hours later.

The best performing clones from the initial screening steps (9 for PnP-HEL23-IgH⁻, 4 for PnP-mRuby-pA) were used for genomic DNA extraction, locus-specific amplification and Sanger sequencing. According to the genomic sequence, one final clone was selected for each cell line.

b. Induction Optimization

After selection of the best clone for each transfected cell line, a second and tighter titration was performed with concentrations in the range between 500 ng/ml and 1.5 µg/ml, and induction measured at different time points (ideally: 24 hrs; 48 hrs; 72 hrs; 96 hrs. Due to Doxycycline having a half-life of 24 hours, it was replaced in culture every 48 hours, as recommended by the manufacturer (Clontech).

For each time point, induction was assessed by:
FACS analysis (GFP)
RT-PCR (mRNA/cDNA)
Western Blot Amplification of AID from cDNA was performed with KAPA HiFi HotStart Ready Mix. For Western Blot, M-PER™ Mammalian Protein Extraction Reagent (Thermo, 78501), supplemented with Halt™ Protease Inhibitor Cocktail (Thermo, 78430) was used to obtain lysates from cultured hybridomas, typically from $10^6$ cells. Anti-Human/Mouse Activation-Induced Cytidine Deaminase (AID) Purified (eBioscience, 14-5959-80) was used as primary antibody for AID detection via WB.

c. iSSHM (AID Activity) Assessment

For the PnP-mRuby-pA-AID cell line, hypermutation activity was first evaluated by FACS analysis and detection of decreasing mRuby fluorescence. For a more thorough evaluation, the mRuby gene was amplified from cDNA and analyzed by sanger or next-generation sequencing (NGS) using the method of molecular amplification fingerprinting (FIG. 12).

For PnP-HEL23-IgH⁻—AID cell line, restored antibody expression and/or antigen-specificity was evaluated by flow cytometry after labelling cells (see previous sections) using anti-IgG2C and anti-IgK (any positivity arisen through random mutations) and HEL-647 (re-gained HEL positivity).

For more definitive assessment and optimization of the system, the iSSHM workflow was repeated for a cell line (obtained by either of the two starting platforms) expressing a functional antibody. To obtain such a situation, PnP-mRuby-pA cells were transfected to exchange mRuby with a sAb donor; PnP-HEL23-IgH⁻—AID cells were transfected to exchange the knocked-out HEL23 sAb with a functional one with the same or another specificity; in an alternative setting, the HEL23 frame was restored by HDR with a 120 ssODN containing a codon-mutated version of the original HCDR3. In case of no previously tested binders, antibodies with a known and testable antigen were typically chosen to evaluate affinity maturation.

Once obtained a PnP-sAb-AID cell line, AID was induced like previously described (ON). After a 48-96 hours induction, Doxycycline was retracted from the system (OFF). To assess affinity maturation, FACS labelling was performed as previously described, but with decreasing antigen concentrations (typically 1-0.001 µg/ml, decreasing ten-fold for each round of analysis/affinity maturation cycle). Positive cells were sorted and underwent a further iSSHM cycle; the cycle was repeated as needed. For each stage of affinity maturation, after Doxycycline retraction from the system, the effective switch OFF was evaluated by monitoring GFP fluorescence by FACS. Once in the OFF state, $V_L$ and $V_H$ regions were amplified from cDNA and iSSHM was evaluated by NGS using the method of molecular amplification fingerprinting.

Generation of the PnP-mRuby2-Cas9 Cell Line

Cloning of the donor cassette for constitutive expression of the Cas9 protein was performed in three steps. (1) The pSpCas9(BB)-2A-Puro vector (pX459) and MDH1-PGK-GFP_2.0 vector were obtained from Addgene (plasmid #48139, #11375, respectively). The Cas9-2A-Puro and GFP gene fragments were obtained from their respective vectors through PCR (KAPA HiFi HotStart ReadyMix) and assembled together with Gibson assembly cloning. (2) Homology arms (1,000 and 976 bp) for the hybridoma's ROSA26 locus were obtained by genomic DNA PCR and assembled with the pUC57(Kan) plasmid backbone through Gibson assembly cloning. (3) Finally, the previously assembled fragments—see points (1 and 2)—were assembled through Gibson assembly cloning. The HDR donor was linearized by restriction digestion with the XhoI and MluI restriction endonucleases followed by gel electrophoresis purification. gRNA-P was cloned as previously described in pX458 (BFP). For the alternative NHEJ insertion design, the Cas9-2A-Puro-GFP construct was linearized without homology arms.

Figure 8:
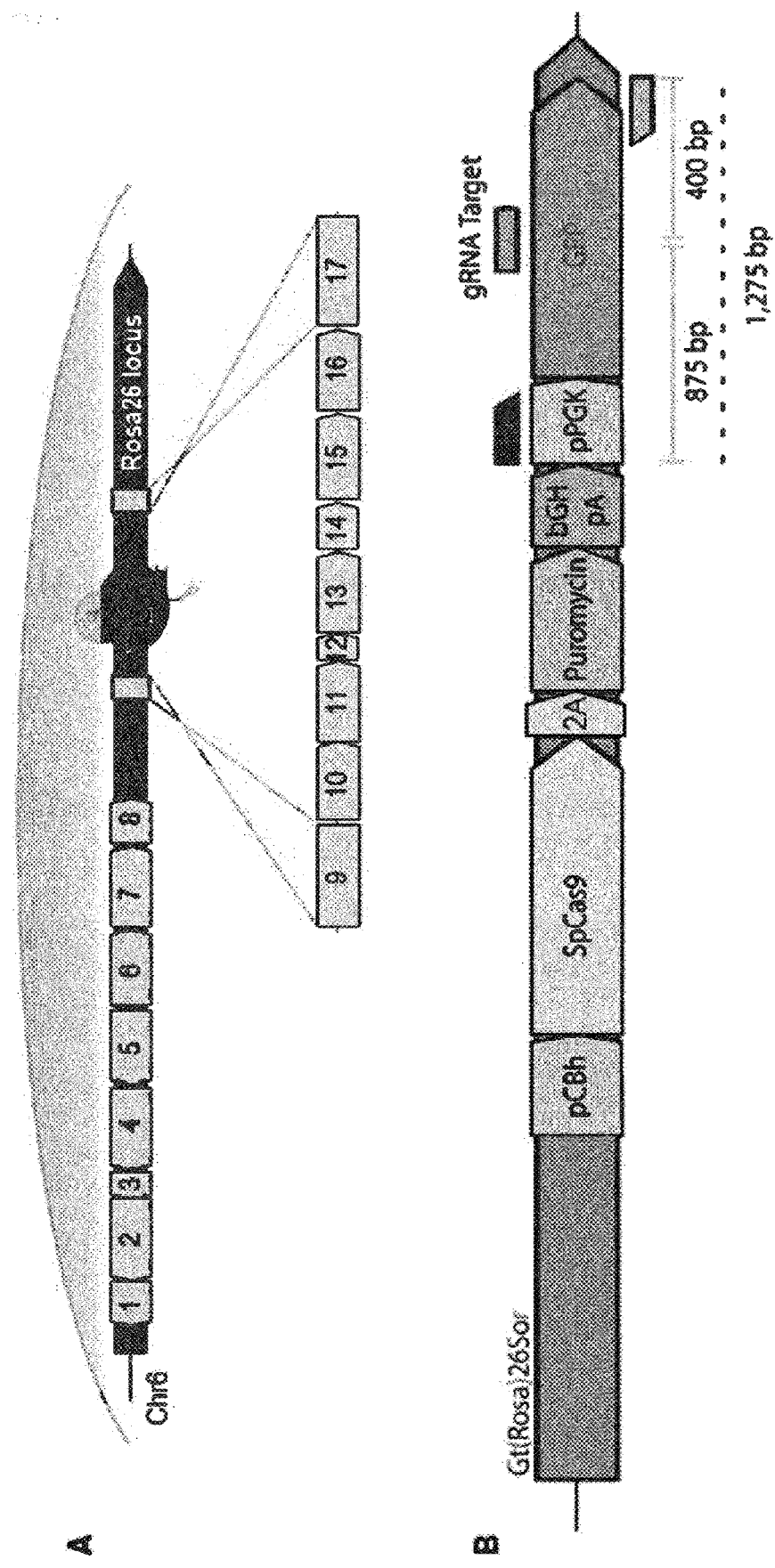
FIG. 8 shows design and validation of PnP-Cas9 cell lines. (A) The ROSA26 locus is targeted for CRISPR-Cas9 induced HDR integration of the constitutive Cas9 cassette. Contained in the cassette are two separate genes. The SpCas9-2A-Puromycin gene with bovine growth hormone (bCGh), the GFP gene is under transcriptional control of the murine pPGK promoter. The 5' and 3' homology arms are also present in the construct. 1: SV40 pA; 2: AID; 3: F2A; 4: GFP; 5: TRE3Gs promoter; 6: hPGK promoter; 7: Tet-On 3G; 8: SV40 pA; 9: homology arm; 10: pCAG promoter; 11: SpCas9; 12: T2A; 13: Puromycin; 14: bGH pA; 15: mPGK promoter; 16: GFP; 17: homology arm. (B) A close up of the Cas9 donor construct, shown are guide RNA target sites within GFP or pPGK, which are used to subsequently inactivate GFP by Cas9-induced NHEJ. (C) Sanger sequencing results before or after introduction of guide RNA in PnPCas9. (D) The T7E1 assay confirms that PnP-Cas9 cells in the presence of guide RNA lead to Cas9-induced NHEJ of GFP cells. (E) Flow cytometry plots show that in PnP-mRuby-Cas9 cells, the addition of gRNA targeting mRuby leads to knockout of mRuby expression in nearly all cells.
Figure 8:
Figure 8:
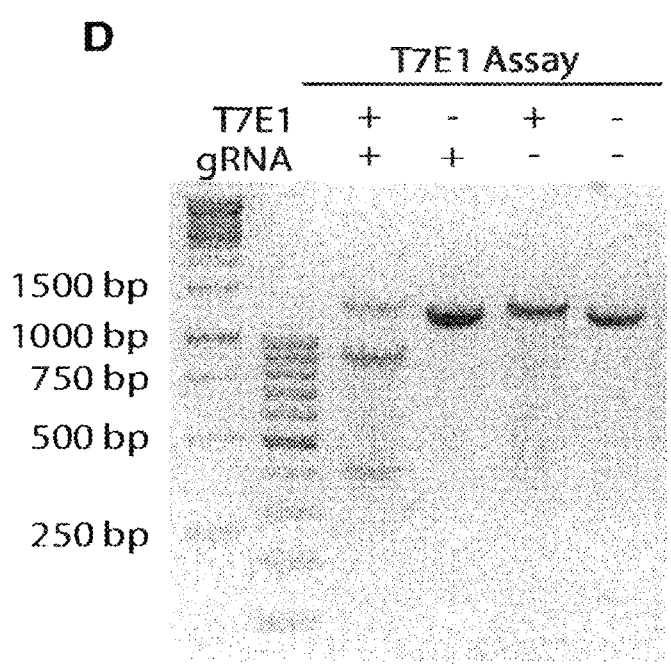
Figure 8:
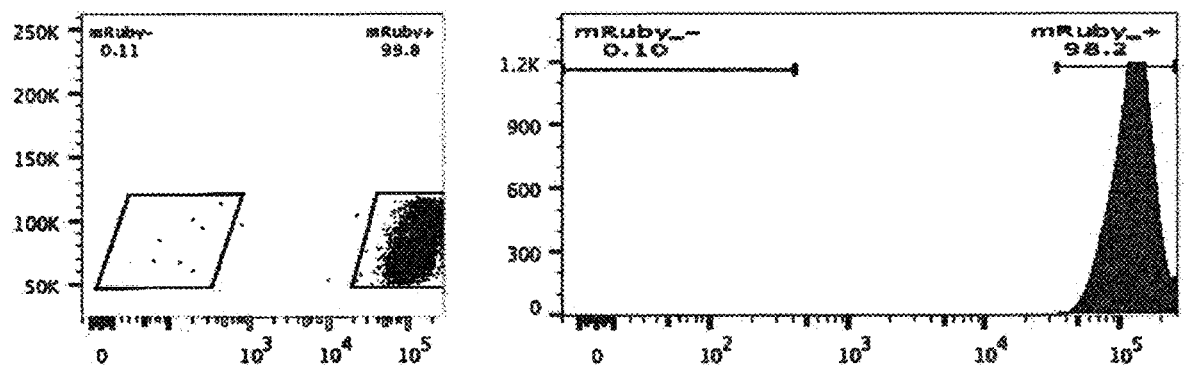
Figure 8:
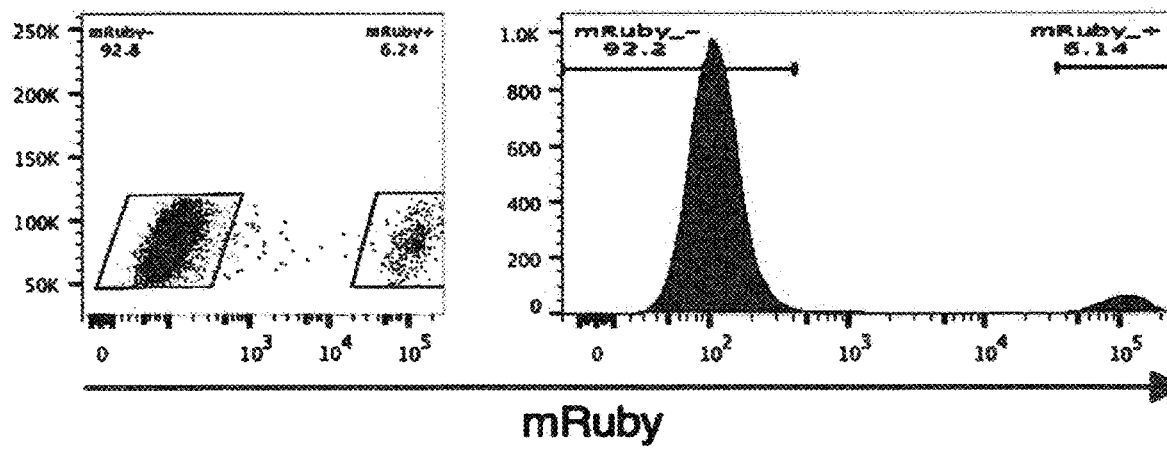

Following transfection with the Cas9-2A-Puro-GFP donor, GFP⁺ cells were sorted and expanded. Cells were then selected for stable integration of the donor construct by culturing in regular growth media supplemented with 2.5 µg/ml of Puromycin (Thermo, A1113802) for up to one week before single-cell isolation, growth and PCR characterization. After identification of a single clone with correct integration of the Cas9-2A-Puro-GFP cassette, Cas9 activity within the cell was validated through transfection of a guide RNA targeting GFP. Cas9 cleavage activity was validated by T7E1 assay and Sanger sequencing of PCR amplicons (FIG. 8). GFP knock out effectiveness was confirmed by flow cytometry.

The cell lines engineered for constitutive Cas9 expression are: PnP-mRuby-pA; PnP-HEL23-IgH⁻. A more comprehensive cell line was designed to incorporate both the constitutive Cas9 and the inducible AID; due to the constructs bearing homology with two different regions of the ROSA26 locus, it was possible to incorporate them in tandem like shown in FIG. 8A. This allowed us to merge the high HDR efficiency achieved by constitutively expressing Cas9 with the iSSHM workflow.

Cas9 Cells—In Vitro Transcription of Guide RNA or Synthetic Oligonucleotides (IDT)

The PnP-mRuby-Cas9 cell line, constitutively expressing Cas9, was transfected with the 10 appropriate HDR donor and already transcribed guide RNAs. The latter were obtained as oligonucleotides from IDT or in vitro transcribed. In the case of in vitro transcription, the previously described guide-DNA oligodeoxynucleotides (see Cloning and assembly CRISPR-Cas9 targeting constructs section) served as templates for the MEGAscript® T7 transcription kit (Thermo, AM1334). An adapted protocol was as described previously (https://www.protocols.io/view/In-vitro-transcription-of-guide-RNAs-d4w8xd?step=3 accessed Feb. 21, 2017).

The invention claimed is:

1. A recombinant mammalian B cell line comprising:
an expressed transgenic genomic DNA sequence inserted into an endogenous immunoglobulin locus comprised in the mammalian B cell, wherein the transgenic genomic DNA sequence comprises:
(a) a nucleic acid that encodes a protein of interest that is not endogenous to the mammalian B cell, wherein the protein of interest is expressed under the control of an endogenous immunoglobulin promoter; and
(b) two homology arms corresponding to the endogenous immunoglobulin locus;
wherein the endogenous immunoglobulin locus is knocked out;
wherein the recombinant mammalian B cell is genetically modified to transiently or constitutively express a nucleic acid encoding a CRISPR-associated endonuclease (Cas9), and
wherein the CRISPR-Cas9 is expressed under the control of a non-immunoglobulin promoter, or a constitutive promoter.

2. The recombinant mammalian B cell of claim 1, wherein the nucleic acid encodes a marker protein and wherein the marker protein is a fluorescent protein comprising a guide RNA target site that is amenable to cleavage by the CRISPR-associated endonuclease (Cas9).

3. The recombinant mammalian B cell according to claim 2, wherein in the recombinant mammalian B cell, the endogenous VH gene and the endogenous VL gene are disrupted.

4. The recombinant mammalian B cell according to claim 2, wherein the recombinant mammalian B cell is a human cell.

5. A plurality of recombinant mammalian B cells comprising:
(a) an inducible synthetic somatic hypermutation (iS-SHM) system comprising an activation-induced cytidine deaminase (AID) driven by an inducible promoter; and
(b) a transgenic genomic DNA sequence encoding a protein of interest that is not endogenous to a mammalian B cell,
wherein each member of the plurality of recombinant mammalian B cells comprises a transgenic genomic DNA sequence encoding a variant of the protein of interest,
wherein the transgenic genomic DNA sequence is inserted into an endogenous immunoglobulin locus comprised in the recombinant mammalian B cell, and the endogenous immunoglobulin locus is knocked out; and
wherein each variant of the protein of interest expressed by a member of the plurality of recombinant mammalian B cells is different from any other variant of the protein of interest expressed by another member of the plurality of recombinant mammalian B cells.

6. The plurality of recombinant mammalian B cells according to claim 5, wherein each variant is different from another variant in one to five positions of its amino acid sequence.

7. The plurality of recombinant mammalian B cells according to claim 5, wherein each variant is at least 80%, 85%, 90%, 95%, 97%, 98% or 99% identical to any another variant encoded by a member of the plurality.

8. The recombinant mammalian B cell according to claim 1, wherein the recombinant B cell is selected from the group consisting of a primary B cell, an immortalized B cell, a hybridoma cell, a myeloma cell, a plasmacytoma cell, and a lymphoma cell.

9. The recombinant mammalian B cell according to claim 1, wherein the recombinant mammalian B cell is genetically modified to express a safe harbor locus.

10. The recombinant mammalian B cell according to claim 9, wherein the recombinant mammalian B cell is genetically modified to constitutively express the CRISPR-associated endonuclease (Cas9), and wherein the CRISPR-associated endonuclease is inserted into the safe harbor locus.

11. The recombinant mammalian B cell according to claim 1, wherein the recombinant mammalian B cell is genetically modified to express an activation-induced cytidine deaminase (AID) in an inducible and titratable manner.

12. The recombinant mammalian B cell according to claim 11, wherein the activation-induced cytidine deaminase (AID) is integrated into a safe harbor locus or into a native AID locus.

13. The recombinant mammalian B cell according to claim 11, wherein the AID is expressed under an inducible promoter.

14. The recombinant mammalian B cell according to claim 13, wherein the inducible promoter is a TRE3GS promoter.

15. The recombinant mammalian B cell according to claim 1, wherein the recombinant mammalian B cell comprises an expression cassette comprising a TRE3GS promoter, a DNA sequence encoding an activation-induced cytidine deaminase (AID), a human phosphoglycerate kinase 1 promoter (hPGK), a Tet-On 3G transactivator protein, and a SV40 poly-A signal.

16. The recombinant mammalian B cell according to claim 13, wherein the inducible expression of the AID generates multiple genomic mutations within the protein of interest by inducible synthetic somatic hypermutation (iS-SHM).

17. The recombinant mammalian B cell according to claim 1, wherein the protein of interest is selected from the group consisting of:
(a) a full-length antibody, a synthetic antigen binding fragment, a humanized camelide antibody, an immunoglobulin antigen-binding fragment, or a full-length antibody comprising a synthetic antigen binding fragment (sFAb);
(b) a designed ankyrin repeat protein; and
(c) a polypeptide comprising an armadillo repeat, a leucine-rich repeat, a tetratricopeptide repeat, a protein A domain, a fibronectin domain FN3, a consensus fibronectin domain, a lipocalin domain, a Zinc finger domain, a Src homology domain 2 (SH2), a Src homology domain 3 (SH3), a PDZ domain, a gamma-crystallin domain, a ubiquitin domain, a cysteine knot domain, or a knottin domain.

18. The recombinant mammalian B cell according to claim 9, wherein the safe harbor locus is selected from a murine Rosa26 locus or an AAVS1 locus.

19. The recombinant mammalian B cell according to claim 1, wherein the recombinant mammalian B cell further comprises one or more randomized nucleic acid sequences that are homologous to one or more regions of the protein of interest, and wherein the one or more randomized nucleic acid sequences comprise a donor dsDNA, a donor ssDNA, degenerate nucleotides, or trinucleotide codons.

20. The recombinant mammalian B cell according to claim 1, wherein the endogenous immunoglobulin promoter is a $V_H$ promoter.

* * * * *